United States Patent
Sorensen et al.

(10) Patent No.: US 11,667,711 B2
(45) Date of Patent: Jun. 6, 2023

(54) ANTI-HUMAN LAG-3 ANTIBODIES AND THEIR USE IN IMMUNOHISTOCHEMISTRY (IHC)

(71) Applicant: Agilent Technologies, Inc., Santa Clara, CA (US)

(72) Inventors: Morten Draeby Sorensen, Herlev (DK); Tine Hagedorn-Olsen, Skibby (DK)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 17/331,344

(22) Filed: May 26, 2021

(65) Prior Publication Data

US 2021/0371520 A1 Dec. 2, 2021

Related U.S. Application Data

(60) Provisional application No. 63/030,873, filed on May 27, 2020.

(51) Int. Cl.
*C07K 16/00* (2006.01)
*C07K 16/28* (2006.01)
*G01N 33/574* (2006.01)

(52) U.S. Cl.
CPC ... *C07K 16/2803* (2013.01); *G01N 33/57492* (2013.01); *C07K 2317/24* (2013.01); *C07K 2317/51* (2013.01); *C07K 2317/515* (2013.01); *C07K 2317/52* (2013.01); *C07K 2317/56* (2013.01); *G01N 2333/70503* (2013.01)

(58) Field of Classification Search
CPC .......... G01N 33/57492; C07K 2317/24; C07K 2317/51; C07K 2317/515; C07K 2317/52; C07K 2317/56
See application file for complete search history.

(56) References Cited

U.S. PATENT DOCUMENTS

2016/0310570 A1   10/2016   Triebel

FOREIGN PATENT DOCUMENTS

| KR | 10-2018-0042412 A | 4/2018 |
|----|-------------------|--------|
| WO | WO 2010-019570 A2 | 2/2010 |
| WO | WO 2019-009728 A1 | 1/2019 |
| WO | WO 2019-046225 A1 | 3/2019 |

OTHER PUBLICATIONS

PCT Search Report for PCT Application No. PCT/US2021/034278, filed May 26, 2021.
Puhr et al., "New emerging targets in cancer immunotherapy: the role of LAG3" ESMO Open, 2019, v 4, e000482, p. 1-6.
Long et al., "The promising immune checkpoint LAG-3: from tumor microenvironment to cancer immunotherapy" Genes & Cancer, 20218, v 9, p. 176-189.
International Preliminary Report on Patentability for PCT Application No. PCT/US2021/034278, dated Dec. 8, 2022.

*Primary Examiner* — Lei Yao
(74) *Attorney, Agent, or Firm* — ArentFox Schiff LLP

(57) ABSTRACT

Provided are chimeric or recombinant antibodies (Ab), or antigen binding fragments thereof, or monomeric or dimeric antigen binding proteins, that can specifically bind to human LAG-3 polypeptides, including human LAG-3 polypeptides expressed on the surface of lymphocytes such as activated T cells that have infiltrated tumors or tumor infiltrating lymphocytes (TILs), and methods for making and using them. In alternative embodiments, chimeric or a recombinant antibodies (Ab), or antigen binding fragments thereof, or monomeric or dimeric antigen binding proteins as provided herein are used for in vitro diagnostics, for example, in immunohistochemistry (IHC), for example, to diagnose and/or treat a cancer, for example, bladder cancer, urothelial carcinoma, breast cancer, lung cancer, Non-Small Cell Lung Cancer, renal carcinoma, Renal Clear cell Carcinoma and/or melanoma or malignant melanoma, by their ability to specifically bind to activated T cells that have infiltrated tumors, or tumor infiltrating lymphocytes.

22 Claims, 20 Drawing Sheets
(20 of 20 Drawing Sheet(s) Filed in Color)

Specification includes a Sequence Listing.

ANTI-HUMAN LAG-3 ANTIBODIES AND THEIR USE IN IMMUNOHISTOCHEMISTRY (IHC)

RELATED APPLICATIONS

This U.S. utility patent application claims the benefit of priority under 35 U.S.C. § 119(e) to U.S. Provisional Patent Application Ser. No. (USSN) 63/030,873, filed May 27, 2020. The aforementioned application is expressly incorporated herein by reference in its entirety and for all purposes.

TECHNICAL FIELD

This invention generally relates to immunohistochemistry (IHC) and cancer diagnosis and treatment. In alternative embodiments, provided are chimeric or a recombinant antibodies (Ab), or antigen binding fragments thereof, or monomeric or dimeric antigen binding proteins, that can specifically bind to human LAG-3 polypeptides, including human LAG-3 polypeptides expressed on the surface of lymphocytes such as activated T cells that have infiltrated tumors, or human LAG-3 polypeptides expressed on tumor infiltrating lymphocytes (TILs). In alternative embodiments, provided are products of manufacture and kits comprising chimeric or a recombinant Abs, or antigen binding fragments thereof, or monomeric or dimeric antigen binding proteins as provided herein, or nucleic acids encoding them, or cells expressing them, and methods for making and using them. In alternative embodiments, chimeric or a recombinant antibodies (Ab), or antigen binding fragments thereof, or monomeric or dimeric antigen binding proteins as provided herein are used for in vitro diagnostics, for example, by immunohistochemistry (IHC). In alternative embodiments, chimeric or a recombinant antibodies (Ab), or antigen binding fragments thereof, or monomeric or dimeric antigen binding proteins, as provided herein are used in IHC protocols to diagnose and/or treat a cancer, for example bladder cancer, urothelial carcinoma, a breast cancer, a lung cancer, a renal cell carcinoma, a Renal Clear cell Carcinoma (RCC), and/or a melanoma or a malignant melanoma, by their ability to specifically bind to activated T cells that have infiltrated tumors, or tumor infiltrating lymphocytes (TILs).

BACKGROUND

The Lymphocyte-Activation Gene 3, or LAG-3 (or LAG3), protein, is encoded by the LAG3 gene and is also known as CD223. LAG-3 is expressed on various lymphoid cells types. It is a T cell activation marker and is expressed on both CD4 and CD8 T cells, 3 to 4 days post activation [1]. Additionally, LAG-3 is expressed on activated natural killer (NK) cells and plasmacytoid dendritic cells [2].

LAG-3-expressing lymphoid cells such as tumor infiltrating lymphoid cells has been found in a variety of human tumors such as melanoma, NSCLC, colorectal cancer, breast cancer, hepatocellular carcinoma, follicular lymphoma, head and neck squamous cell carcinoma, renal cancer, which is significantly associated with aggressive tumor progression and clinicopathological characteristics [3-17].

SUMMARY

In alternative embodiments, provided are chimeric or a recombinant antibodies (Abs), or an antigen (Ag) binding fragments thereof, or a monomeric or dimeric antigen binding protein, capable of specifically binding to a human Lymphocyte-Activation Gene 3 (LAG-3) polypeptide, including human LAG-3 polypeptides expressed on the surface of lymphocytes such as activated T cells that have infiltrated tumors, or human LAG-3 polypeptides expressed on tumor infiltrating lymphocytes (TILs), wherein the chimeric or a recombinant antibody (Ab), or the antigen binding fragment thereof, or the monomeric or dimeric antigen binding protein, specifically binds to a peptide or polypeptide, or an epitope, comprising or consisting of an amino acid sequence:

(SEQ ID NO: 1)
GPPAAAPGHPLAPGPHPAAPSSWGPRPRR.

In alternative embodiments, the chimeric or recombinant antibodies (Ab), or antigen binding fragments thereof, or monomeric or dimeric antigen binding proteins, are fabricated as or in the form of:

an antigen-binding fragment (Fab, or an Ab fragment having just one constant and one variable domain of each of an Ab heavy and light chain), a F(ab')$_2$ (or an Ab digested by pepsin yielding two fragments: a F(ab')$_2$ fragment and a pFc' fragment), a Fab' (a single chain of a F(ab)$_2$ fragment), a single-chain variable fragment (scFv) (or a fusion protein of a variable region of an Ab heavy and light chain connected together with a linker peptide optionally of about ten to about 25 amino acids in length), a (scFv)$_2$, or a di-scFv or a bi-scFv, or a single peptide chain having two variable heavy and two variable light regions yielding tandem scFv, a minibody (or a fusion protein of a variable region of an Ab heavy and light chain connected together with an alkyl group, optionally a methyl or an ethyl group)

a diabody (or an scFv with a linker peptide too short (optionally about five amino acids) for the two variable regions to fold together forcing the scFvs to dimerize), a triabody or a tetrabody (or an scFv with a linker peptide too short (optionally about one or two amino acids) for the two variable regions to fold together forcing the scFvs to trimerize or tetramize), a single-domain antibody (dAB) (or a single variable region of an Ab heavy or Ab light chain), a plurality of complementarity determining region (CDR) fragments, or a multispecific antibody formed from two or more antibody fragments.

In alternative embodiments of the chimeric or recombinant antibodies (Ab), or antigen binding fragments thereof, or monomeric or dimeric antigen binding proteins as provided herein:

the sequence of the heavy chain variable region is or comprises:

(SEQ ID NO: 2)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSS;

the sequence of the light chain variable region is or comprises:

(SEQ ID NO: 3)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVK;

the sequence of the heavy chain variable region is or comprises:

(SEQ ID NO: 2)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSS, and
the sequence of the light chain variable region is or comprises:

(SEQ ID NO: 3)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVK;

- the sequence of the heavy chain variable region comprises SEQ ID NO:2 having at least one, two, three, four, five, six, seven, eight, nine, ten, eleven or twelve conservative amino acid substitutions, wherein the heavy chain variable region capable of specifically binding to the human LAG-3 polypeptide, the amino acid (SEQ ID NO:1), or the epitope when either unpaired (alone) or paired with a light chain variable region;
- the sequence of the light chain variable region comprises SEQ ID NO:3 having at least one, two, three, four, five, six, seven, eight, nine, ten, eleven or twelve conservative amino acid substitutions, wherein the light chain variable region is capable of specifically binding to the human LAG-3 polypeptide, the amino acid (SEQ ID NO:1), or the epitope when either unpaired (alone) or paired with a heavy chain variable region;
- the sequence of the heavy chain variable region has at least about 25%, 30%, 40%, 50%, 60%, 70%, 80%, 85%, 90% or 95% sequence identity to SEQ ID NO:2;
- the sequence of the light chain variable region has at least about 25%, 30%, 40%, 50%, 60%, 70%, 80%, 85%, 90% or 95% sequence identity to SEQ ID NO:3;
- the sequence of the heavy chain variable region and the amino acid sequence SEQ ID NO:2 have a Z score of from about 2 to about 8, of a Z score of at least 8, when aligned using distance matrix alignment;
- the sequence of the light chain variable region and the amino acid sequence SEQ ID NO:3 have a Z score of from about 2 to about 8, of a Z score of at least 8, when aligned using distance matrix alignment;
- the heavy chain variable region comprises: the three CDR1, CDR2 and CDR3 complementarity determining regions (CDRs) of SEQ ID NO:2, or CDR1 amino acid (aa) residues 25-32, CDR2 aa residues 50-56, and CDR3 aa residues 95-101, of SEQ ID NO:2;
- the light chain variable region comprises: the three CDR1, CDR2 and CDR3 complementarity determining regions (CDRs) of SEQ ID NO:3, or CDR1 amino acid (aa) residues 27-34, CDR2 aa residues 52-54, and CDR3 aa residues 91-102, of SEQ ID NO:3;
- the chimeric or recombinant Ab or antigen binding fragments thereof, or monomeric or dimeric antigen binding protein, comprises: (a) a heavy chain variable region comprising: the three CDR1, CDR2 and CDR3 complementarity determining regions (CDRs) of SEQ ID NO:2, or CDR1 amino acid (aa) residues 25-32, CDR2 aa residues 50-56, and CDR3 aa residues 95-101, of SEQ ID NO:2; and (b) a light chain variable region comprising: the three CDR1, CDR2 and CDR3 complementarity determining regions (CDRs) of SEQ ID NO:3, or CDR1 amino acid (aa) residues 27-34, CDR2 aa residues 52-54, and CDR3 aa residues 91-102, of SEQ ID NO:3;
- the antibody heavy chain is an IgM, IgG, IgA or IgE isotype heavy chain, and/or the light chain is a kappa or a lambda light chain;
- the sequence of the light chain constant region is or comprises:

(SEQ ID NO: 4)
GDPGAPTVLIFPPAADQVATGTVTIVCVANKYFPDVTVTWEVDGTTQTTGI

ENSKTPQNSADCTYNLSSTLTLTSTQYNSHKEYTCKVTQGTTSVVQSFNRG

DC,
or (SEQ ID NO: 5)
GDPVAPTVLIFPPAADQVATGTVTIVCVANKYFPDVTVTWEVDGTTQTTGI

ENSKTPQNSADCTYNLSSTLTLTSTQYNSHKEYTCKVTQGTTSVVQSFNRG

DC;

- the sequence of the light chain constant region comprises SEQ ID NO:4 or SEQ ID NO:5 having at least one, two, three, four, five, six, seven, eight, nine, ten, eleven or twelve or more conservative amino acid substitutions, wherein the light chain constant region with the conservative amino acid substitutions is capable of specifically binding to or associating with a heavy chain constant region;
- the sequence of the light chain constant region has at least about 25%, 30%, 40%, 50%, 60%, 70%, 80%, 85%, 90% or 95% sequence identity to SEQ ID NO:4 or SEQ ID NO:5, wherein the light chain constant region is capable of specifically binding to or associating with a heavy chain constant region;
- the sequence of the heavy chain constant region is or comprises:

(SEQ ID NO: 6)
GQPKAPSVFPLAPCCGDTPSSTVTLGCLVKGYLPEPVTVTWNSGTLTNGVR

TFPSVRQSSGLYSLSSVVSVTSSSQPVTCNVAHPATNTKVDKTVAPSTCSK

PTCPPPELLGGPSVFIFPPKPKDTLMISRTPEVTCVVVDVSQDDPEVQFTW

YINNEQVRTARPPLREQQFNSTIRVVSTLPIAHQDWLRGKEEKCKVHNKAL

PAPIEKTISKARGQPLEPKVYTMGPPREELSSRSVSLTCMINGFYPSDISV

EWEKNGKAEDNYKTTPAVLDSDGSYFLYSKLSVPTSEWQRGDVFTCSVMHE

ALHNHYTQKSISRSPGK;

the sequence of the heavy chain constant region comprises SEQ ID NO:6 having at least one, two, three, four, five, six, seven, eight, nine, ten, eleven or twelve or more conservative amino acid substitutions, wherein the heavy chain constant region with the conservative amino acid substitutions is capable of specifically binding to or associating with a light chain constant region;

the sequence of the heavy chain constant region has at least about 25%, 30%, 40%, 50%, 60%, 70%, 80%, 85%, 90% or 95% sequence identity to SEQ ID NO:6, wherein the heavy chain constant region is capable of specifically binding to or associating with a light chain constant region;

the sequence of the antibody light chain comprises (the variable region is underlined):

(SEQ ID NO: 7)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVKGDPGAPTVLIFPPAADQVATGTVTIVCVANKYFPDVTVTW

EVDGTTQTTGIENSKTPQNSADCTYNLSSTLTLTSTQYNSHKEYTCKVTQG

TTSVVQSFNRGDC,
or (SEQ ID NO: 8)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVKGDPVAPTVLIFPPAADQVATGTVTIVCVANKYFPDVTVTW

EVDGTTQTTGIENSKTPQNSADCTYNLSSTLTLTSTQYNSHKEYTCKVTQG

TTSVVQSFNRGDC;

the sequence of the antibody heavy chain comprises (the variable region is underlined):

(SEQ ID NO: 9)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSSGQPKAPSVFPLAPCCGDTPSSTVTLGCLVKGYLPEPVTVTW

NSGTLTNGVRTFPSVRQSSGLYSLSSVVSVTSSSQPVTCNVAHPATNTKVD

KTVAPSTCSKPTCPPPELLGGPSVFIFPPKPKDTLMISRTPEVTCVVVDVS

QDDPEVQFTWYINNEQVRTARPPLREQQFNSTIRVVSTLPIAHQDWLRGKE

EKCKVHNKALPAPIEKTISKARGQPLEPKVYTMGPPREELSSRSVSLTCMI

NGFYPSDISVEWEKNGKAEDNYKTTPAVLDSDGSYFLYSKLSVPTSEWQRG

DVETCSVMHEALHNHYTQKSISRSPGK, the chimeric or recombinant antibody (Ab), or antigen binding fragment thereof, or monomeric or dimeric antigen binding protein further comprises: or is bound to, paired with, associated with, or covalently conjugated to, a detectable agent or a binding moiety;

the detectable agent comprises: an enzyme, a biotin, a fluorescent or chemiluminescent label, a fluorophore, a cyanine such as sulfoindo-cyanine, nile red, rhodamine, perylene, fluorenyl, coumarin, 7-methoxycoumarin (Mca), dabcyl, [2-(4-nitro-2,1,3-benzoxadiazol-7-yl) aminoethyl]trimethylammonium (NBD), Nile blue, Tamra or tetramethylrhodamine (TMR), HRP MAGENTA™ chromogen (Dako Omnis, Agilent), boron-dipyrromethene (BODIPY), or derivatives thereof), a dye, a radioisotope, a quantum dot or photoluminescent aqueous nanocrystal, a hapten or an antibody binding epitope or domain;

the enzyme is a peroxidase, an alkaline phosphatase, or a beta-galactosidase, and the peroxidase can be a horse radish peroxidase (HRP);

the hapten comprises a biotin, theophylline, digoxigenin, carborane, fluorescein or bromodeoxyuridine;

the dye comprises a cyanine dye; or Cy3 or Cy5;

the fluorophore comprises dansyl, fluorescein or carboxyfluorescein (FAM) or 6-FAM; and/or the binding moiety comprises: a glutathione S-transferase (GST) or ligandin tag, a polyhistidine (poly-his) tag, a chitin binding protein (CBP), a STREP-TAG™ or a Trp-Ser-His-Pro-Gln-Phe-Glu-Lys (SEQ ID NO:10) peptide tag, a FLAG tag or DYKDDDDK (SEQ ID NO:11) peptide tag, or a maltose binding protein.

In alternative embodiments, provided are recombinant nucleic acids encoding a chimeric or a recombinant antibody (Ab), or an antigen binding fragment thereof, or a monomeric or dimeric antigen binding protein as provided herein.

In alternative embodiments of recombinant nucleic acids as provided herein:

the recombinant nucleic acid further comprises and is operatively linked to a transcriptional regulatory element, and the transcriptional regulatory element can comprise a promoter, or the promoter is a inducible promoter or a constitutive promoter;

the recombinant nucleic acid further comprises sequence encoding an additional protein or peptide moiety or domain, and the additional protein or peptide moiety or domain can comprise a purification moiety or domain to aid in the purification or isolation of the chimeric or recombinant antibody (Ab), or antigen binding fragment thereof, or monomeric or dimeric antigen binding protein, encoded by the recombinant nucleic acid;

the additional protein or peptide moiety or domain comprises: a glutathione S-transferase (GST) or ligandin tag, a polyhistidine (poly-his) tag, a chitin binding protein (CBP), a STREP-TAG™ or a Trp-Ser-His-Pro-Gln-Phe-Glu-Lys (SEQ ID NO:10) peptide tag, a FLAG tag or DYKDDDDK (SEQ ID NO:11) peptide tag, or a maltose binding protein; and/or the recombinant nucleic acid further comprises sequence encoding a protease cleavage site positioned between the purification moiety or domain and the sequence encoding the chimeric or a recombinant antibody (Ab), or an antigen binding fragment thereof, or a monomeric or dimeric antigen binding protein.

In alternative embodiments, a chimeric or recombinant antibody (Ab) as provided herein comprises:

(a) a light chain as set forth in SEQ ID NO:7 operatively bound to, paired with, associated with, or configured with a heavy chain as set forth in SEQ ID NO: 9, wherein the chimeric or recombinant Ab is capable of selectively binding to a human LAG-3 polypeptide; or (b) a light chain as set forth in SEQ ID NO:8 operatively bound to, paired with, associated with, or configured with a heavy chain as set forth in SEQ ID NO: 9, wherein the chimeric or recombinant Ab is capable of selectively binding to a human LAG-3 polypeptides.

In alternative embodiments, provided are expression cassettes, vectors, recombinant viruses, artificial chromosomes, cosmids or plasmids comprising a recombinant nucleic acid as provided herein.

In alternative embodiments, provided are cells comprising a chimeric or a recombinant antibody (Ab), or an antigen binding fragment thereof, or a monomeric or dimeric antigen binding protein as provided herein, a recombinant nucleic acid as provided herein, or an expression cassette, vector, recombinant virus, artificial chromosome, cosmid or plasmid as provided herein, and the cell can be a bacterial, fungal, mammalian, yeast, insect, avian or plant cell.

In alternative embodiments, provided are methods for generating an polyclonal antibody, or for generating a polyclonal immune serum, that is specific for or specifically binds to a human Lymphocyte-Activation Gene 3 (LAG-3) polypeptide, optionally specifically binds to a LAG-3 polypeptide expressed on the surface of a tumor infiltrating lymphocyte such as a tumor infiltrating activated T cell, the method comprising administering to or immunizing a mammal or an avian species with a peptide or polypeptide, or an epitope, comprising the amino acid sequence:

(SEQ ID NO: 1)
GPPAAAPGHPLAPGPHPAAPSSWGPRPRR.

In alternative embodiments, provided are methods for detecting the presence of a human LAG-3 protein in or on a cell (optionally a lymphocyte, or a tumor infiltrating lymphocyte such as a tumor infiltrating activated T cell), a tissue, an organ or a portion of any of the foregoing, comprising: (a) contacting the cell, tissue or organ or portion of any of the foregoing with a chimeric or recombinant antibody (Ab), or antigen binding fragment thereof, or monomeric or dimeric antigen binding protein as provided herein, or encoded by a recombinant nucleic acid as provided herein, and, (b) detecting specific binding of the chimeric or recombinant antibody (Ab), or antigen binding fragment thereof, or monomeric or dimeric antigen binding protein, with a human LAG-3 polypeptide or a GPPAAAPGHPLAPGPHPAAPSSWGPRPRR (SEQ ID NO:1)-comprising polypeptide in the cell, tissue or organ or portion of any of the foregoing, thereby detecting the presence of a human LAG-3 protein in a cell, a tissue, an organ or a portion of any of the foregoing, comprising contacting the cell, tissue or organ or portion of any of the foregoing.

In alternative embodiments of methods for detecting the presence of a human LAG-3 protein in a cell (optionally a lymphocyte, or a tumor infiltrating lymphocyte such as a tumor infiltrating activated T cell), a tissue, an organ or portion thereof as provided herein:
  the contacting comprises use of an immunohistochemistry (IHC) assay;
  the method further comprises contacting the chimeric or recombinant antibody (Ab), or antigen binding fragment thereof, or monomeric or dimeric antigen binding protein with a detectable agent to indicate or signal the specific binding of the chimeric or recombinant antibody (Ab), or antigen binding fragment thereof, or monomeric or dimeric antigen binding protein to the human LAG-3 protein;
  the detectable agent specifically binds to the chimeric or recombinant antibody (Ab), or antigen binding fragment thereof, or monomeric or dimeric antigen binding protein; or, the detectable agent is or comprises an antibody or an antigen binding fragment or a secondary antibody thereof that specifically binds to the chimeric or recombinant antibody (Ab), or antigen binding fragment thereof, or monomeric or dimeric antigen binding protein which is bound to, paired with, associated with, or configured with the human LAG-3 protein; or, the detectable agent is or comprises an antibody or an antigen binding fragment or a secondary antibody thereof that specifically binds to a hapten or tag attached or conjugated to the chimeric or recombinant antibody (Ab) or antigen binding fragment thereof, or monomeric or dimeric antigen binding protein; and/or
  the antibody or an antigen binding fragment or the secondary antibody further comprises or has attached or conjugated thereto a second detectable agent or an enzyme, and the enzyme can be an alkaline phosphatase, a beta-galactosidase or a peroxidase; or, the antibody or an antigen binding fragment or the secondary antibody further comprises or has attached or conjugated thereto a biotin, a fluorescent or chemiluminescent label, a fluorophore, a cyanine such as sulfoindo-cyanine, nile red, rhodamine, perylene, fluorenyl, coumarin, 7-methoxycoumarin (Mca), dabcyl, [2-(4-nitro-2,1,3-benzoxadiazol-7-yl)aminoethyl]trimethylammonium (NBD), Nile blue, Tamra or tetramethylrhodamine (TMR), HRP MAGENTA™ chromogen (Dako Omnis, Agilent), boron-dipyrromethene (BODIPY), or derivatives thereof), a dye, a radioisotope, a quantum dot or photoluminescent aqueous nanocrystal, a hapten; and the dye can comprise a cyanine dye, or Cy3 or Cy5; or, the hapten comprises a biotin, theophylline, digoxigenin, carborane, fluorescein or bromodeoxyuridine.

In alternative embodiments, provided are methods for detecting or diagnosing a LAG-3 protein-expressing cancer, or a cancer tissue having contained therein a LAG-3 expressing lymphocyte, or a LAG-3 expressing tumor infiltrating lymphocyte such as a tumor infiltrating activated T cell, comprising: detecting the expression or presence of a human LAG-3 protein in a cell, tissue or organ sample or portion thereof by contacting the cell, tissue or organ sample with a chimeric or recombinant antibody as provided herein, or encoded by a recombinant nucleic acid as provided herein, and detecting whether or not the chimeric or recombinant antibody specifically binds to a human LAG-3 protein in the cell, tissue or organ sample or portion thereof, and the detecting of specific binding indicates the expression or presence of the human LAG-3 protein in the cell, tissue or organ sample, or portion thereof.

In alternative embodiments of methods for detecting or diagnosing a LAG-3 protein-expressing cancer, or a cancer tissue having contained therein a LAG-3 expressing lymphocyte, or a LAG-3 expressing tumor infiltrating lymphocyte such as a tumor infiltrating activated T cell, as provided herein:
  the cell is an activated T cell, an activated T cell that has infiltrated a tumor, or a tumor infiltrating lymphocyte (TIL);
  the detecting of specific binding indicates the expression or presence of the human LAG-3 protein in the cell, tissue or organ sample, or portion thereof, thereby diagnosing or detecting the cancer;
  the cancer is selected from the group consisting of: a renal cell carcinoma, a Renal Clear cell Carcinoma (RCC), adenocarcinoma, bladder cancer, urothelial carcinoma, a breast cancer or a mammary carcinoma or ductal carcinoma in situ (DCIS), a carcinoid, Hodgkin's Lymphoma, chronic lymphocytic leukemia, colorectal cancer, ovarian cancer, kidney cancer or renal cell carcinoma, liver cancer or hepatocellular carcinoma, stomach or gastric cancer, lymphoma or follicular lymphoma, prostate cancer, head and neck squamous cell carcinoma, a lung cancer, a Non-Small Cell Lung Cancer (NSCLC), mesothelioma or malignant pleural mesothelioma, anal squamous cell carcinoma, pancreatic cancer, and melanoma or malignant melanoma; and, the adenocarcinoma can be a lung adenocarcinoma or a colon adenocarcinoma;

the detection comprises using or conducting an immunohistochemistry (IHC) assay or a flow cytometry;

the conducting or using of the flow cytometry comprises use of a fluorescence-activated cell sorter (FACS) or an impedance flow cytometer; and/or the cell, tissue or organ sample or portion thereof is or is derived from a biopsy from a patient.

In alternative embodiments, provided are methods for treating, ameliorating or preventing a cancer comprising first detecting or diagnosing the cancer in an individual in need thereof using a method as provided herein, followed by treatment of the individual in need thereof.

In alternative embodiments of methods for treating, ameliorating or preventing a cancer the cancer is selected from the group consisting of: bladder cancer, urothelial carcinoma, a breast cancer or a mammary carcinoma or a ductal carcinoma in situ (DCIS), a lung cancer, a Non-Small Cell Lung Cancer (NSCLC), a renal cell carcinoma, a Renal Clear cell Carcinoma (RCC), an adenocarcinoma, a mammary carcinoma or a ductal carcinoma in situ (DCIS), a carcinoid, Hodgkin's Lymphoma, chronic lymphocytic leukemia, colorectal cancer, ovarian cancer, kidney cancer, liver cancer or hepatocellular carcinoma, stomach or gastric cancer, lymphoma or follicular lymphoma, prostate cancer, head and neck squamous cell carcinoma, mesothelioma or malignant pleural mesothelioma, anal squamous cell carcinoma, pancreatic cancer, and melanoma or malignant melanoma.

In alternative embodiments, provided are uses of a chimeric or a recombinant antibody (Ab), or an antigen binding fragment thereof, or a monomeric or dimeric antigen binding protein as provided herein, or encoded by a recombinant nucleic acid as provided herein, for detecting or diagnosing a cancer, or a cancer tissue having contained therein a LAG-3 expressing lymphocyte, or a LAG-3 expressing tumor infiltrating lymphocyte such as a tumor infiltrating activated T cell, or treating, ameliorating or preventing the cancer.

In alternative embodiments, provided are chimeric or a recombinant antibodies (Abs), or an antigen binding fragments thereof, or a monomeric or dimeric antigen binding proteins as provided herein, or encoded by a recombinant nucleic acid as provided herein, for use in detecting or diagnosing a cancer, or a cancer tissue having contained therein a LAG-3 expressing lymphocyte, or a LAG-3 expressing tumor infiltrating lymphocyte such as a tumor infiltrating activated T cell, or treating, ameliorating or preventing the cancer.

In alternative embodiments, provided are kits comprising a chimeric or a recombinant antibody (Ab), or an antigen binding fragment thereof, or a monomeric or dimeric antigen binding protein as provided herein, or encoded by a recombinant nucleic acid as provided herein. In alternative embodiments the kits as provided herein comprise components needed for an immunohistochemistry (IHC) assay; and/or, instructions for practicing a method as provided herein. In alternative embodiments of the kits as provided herein the chimeric or the recombinant antibody (Ab), the antigen binding fragment thereof, or the monomeric or dimeric antigen binding protein, is substantially purified or isolated.

In alternative embodiments, provided are products of manufacture comprising a chimeric or a recombinant antibody (Ab), or an antigen binding fragment thereof, or a monomeric or dimeric antigen binding protein as provided herein, or encoded by a recombinant nucleic acid as provided herein. In alternative embodiments, the products of manufacture comprise or is fabricated as or manufactured as a slide, a well, a chip, a biochip, an array, a tray, a dish or a microtiter plate or dish. In alternative embodiments, of the products of manufacture, the chimeric or the recombinant antibody (Ab), the antigen binding fragment thereof, or the monomeric or dimeric antigen binding protein, is substantially purified or isolated, or is in the form of an unpurified or partially purified culture supernatant.

In alternative embodiments, provided are phages or phagemids comprising or expressing on its surface a chimeric or a recombinant antibody (Ab), or an antigen binding fragment thereof, or a monomeric or dimeric antigen binding protein as provided herein, or encoded by a recombinant nucleic acid as provided herein.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The patent or application file contains at least one drawing executed in color. Copies of this patent or patent application publication with color drawing(s) will be provided by the Office upon request and payment of the necessary fee.

The drawings set forth herein are illustrative of exemplary embodiments provided herein and are not meant to limit the scope of the invention as encompassed by the claims.

Figures are described in detail herein.

Figure 1:
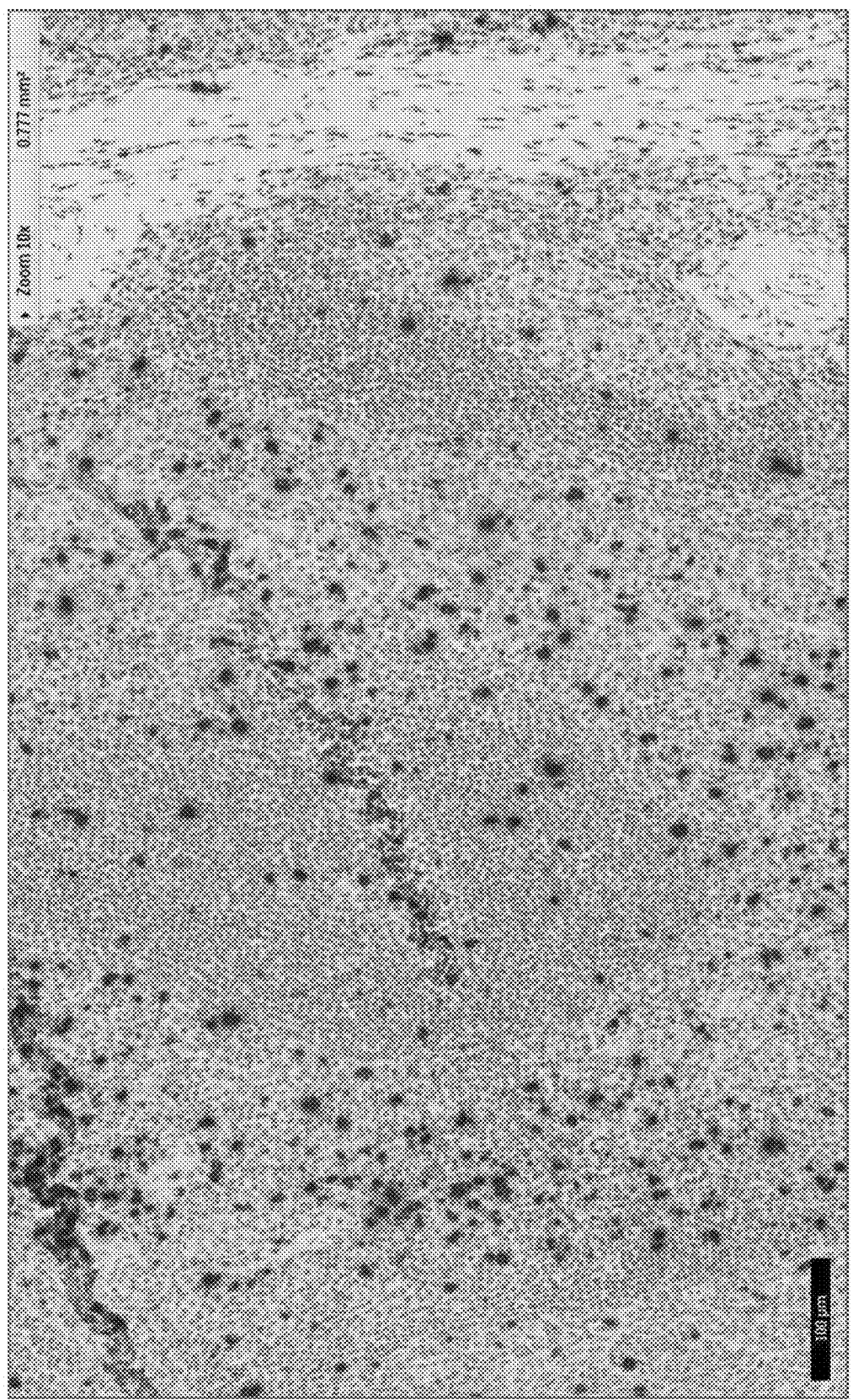

FIG. 1 illustrates an image of staining a tonsil using super sensitive IHC using a cell culture supernatant of the exemplary clone 12H8.

Figure 2:
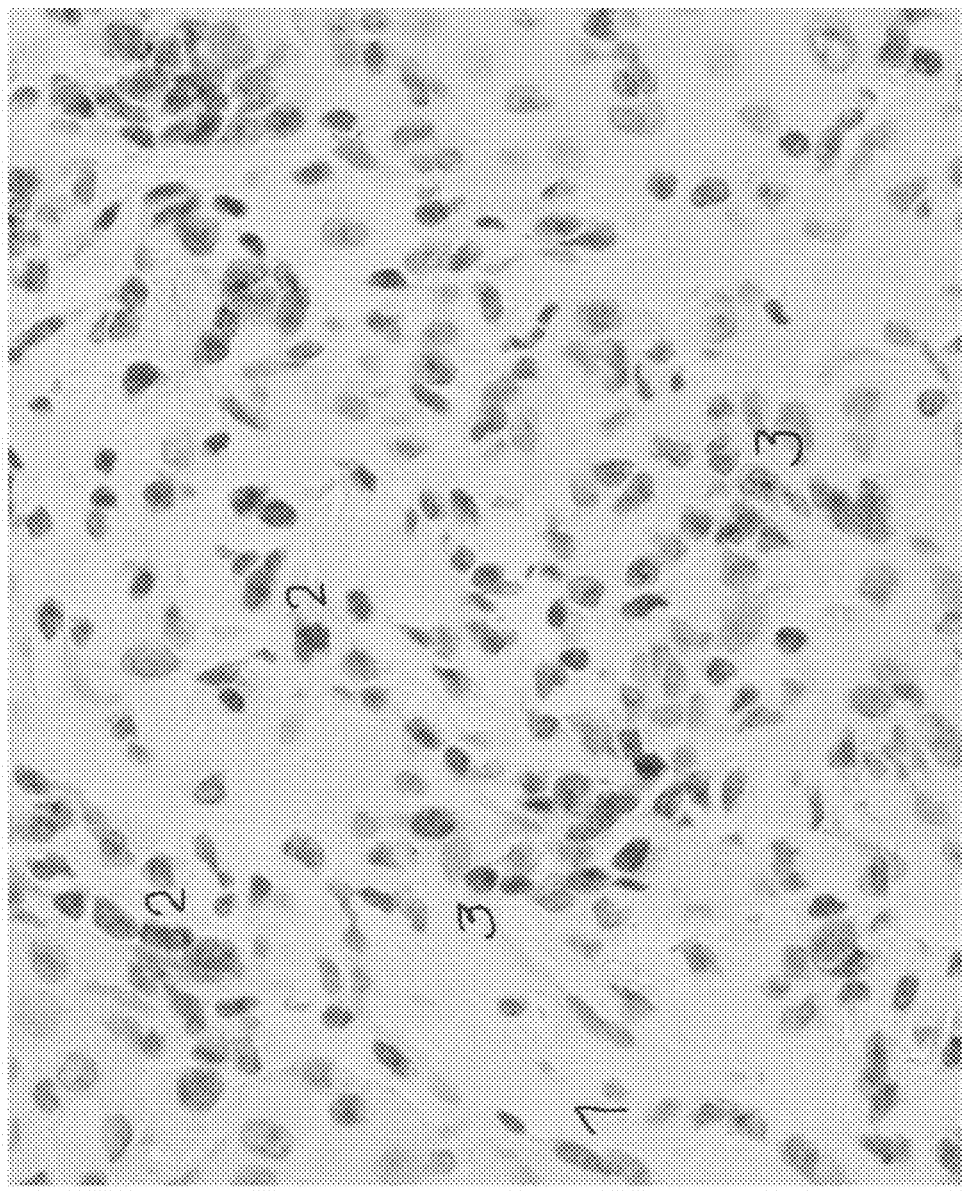
Figure 3A:
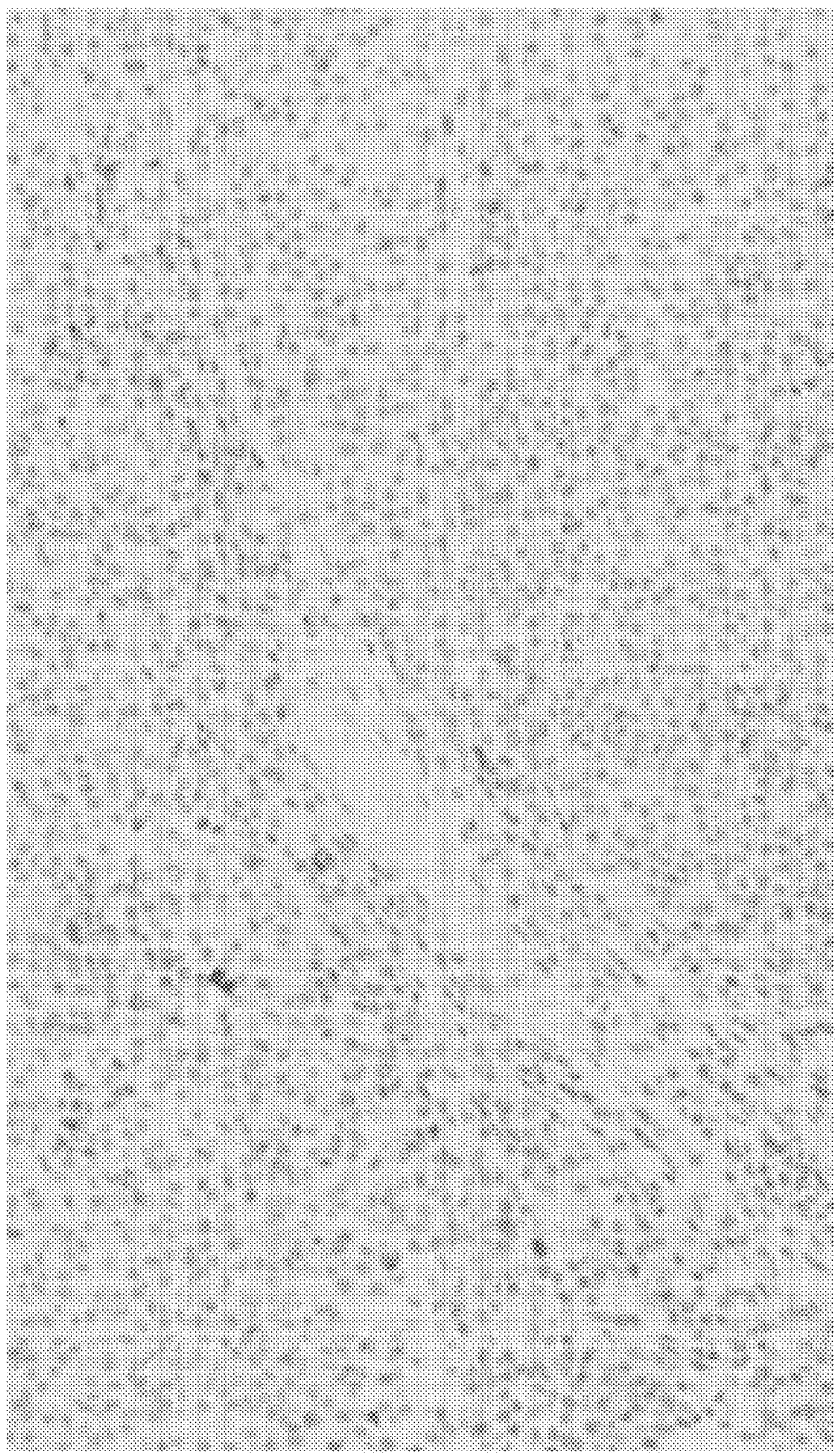
Figure 3B:
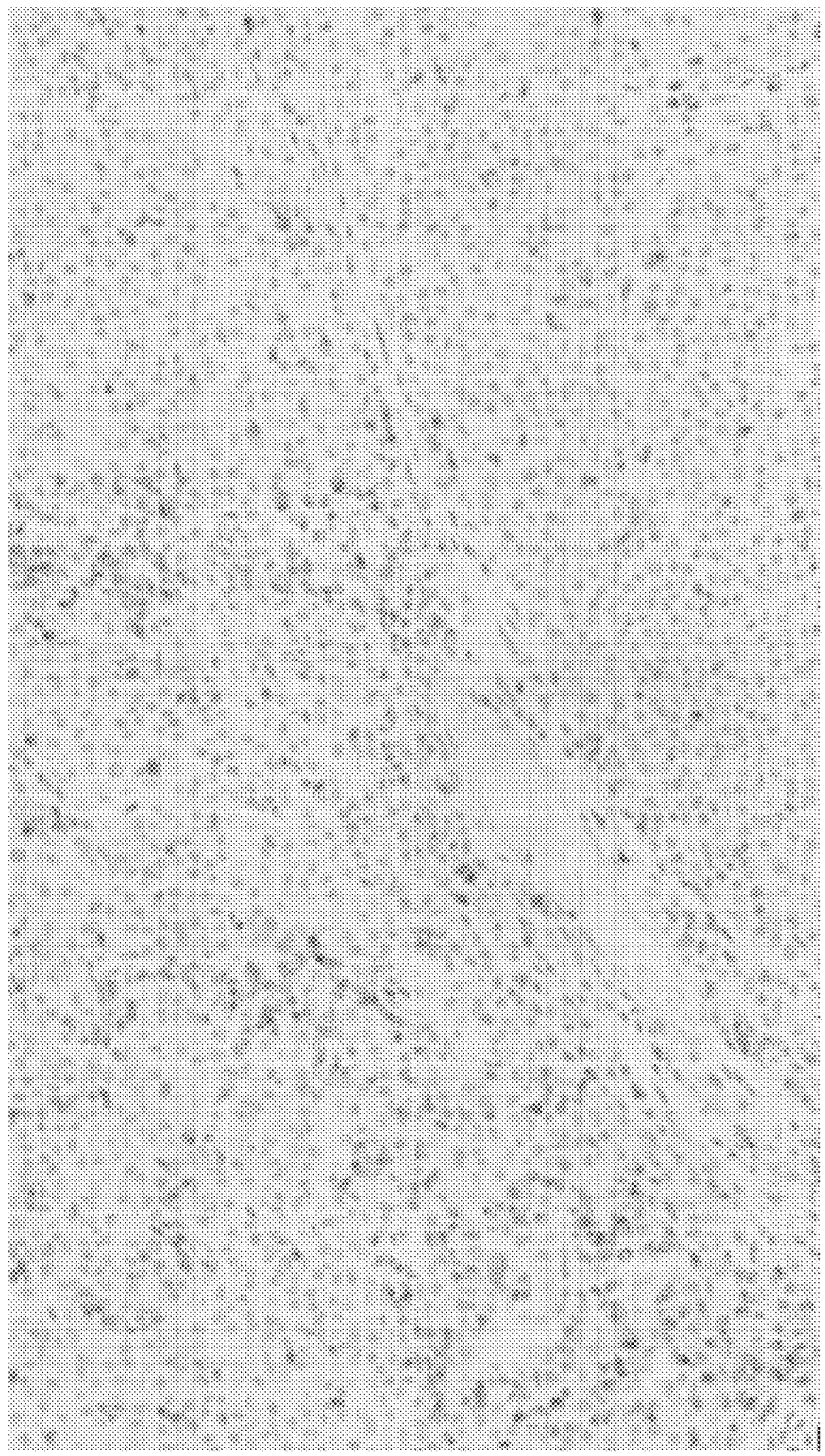
Figure 4A:
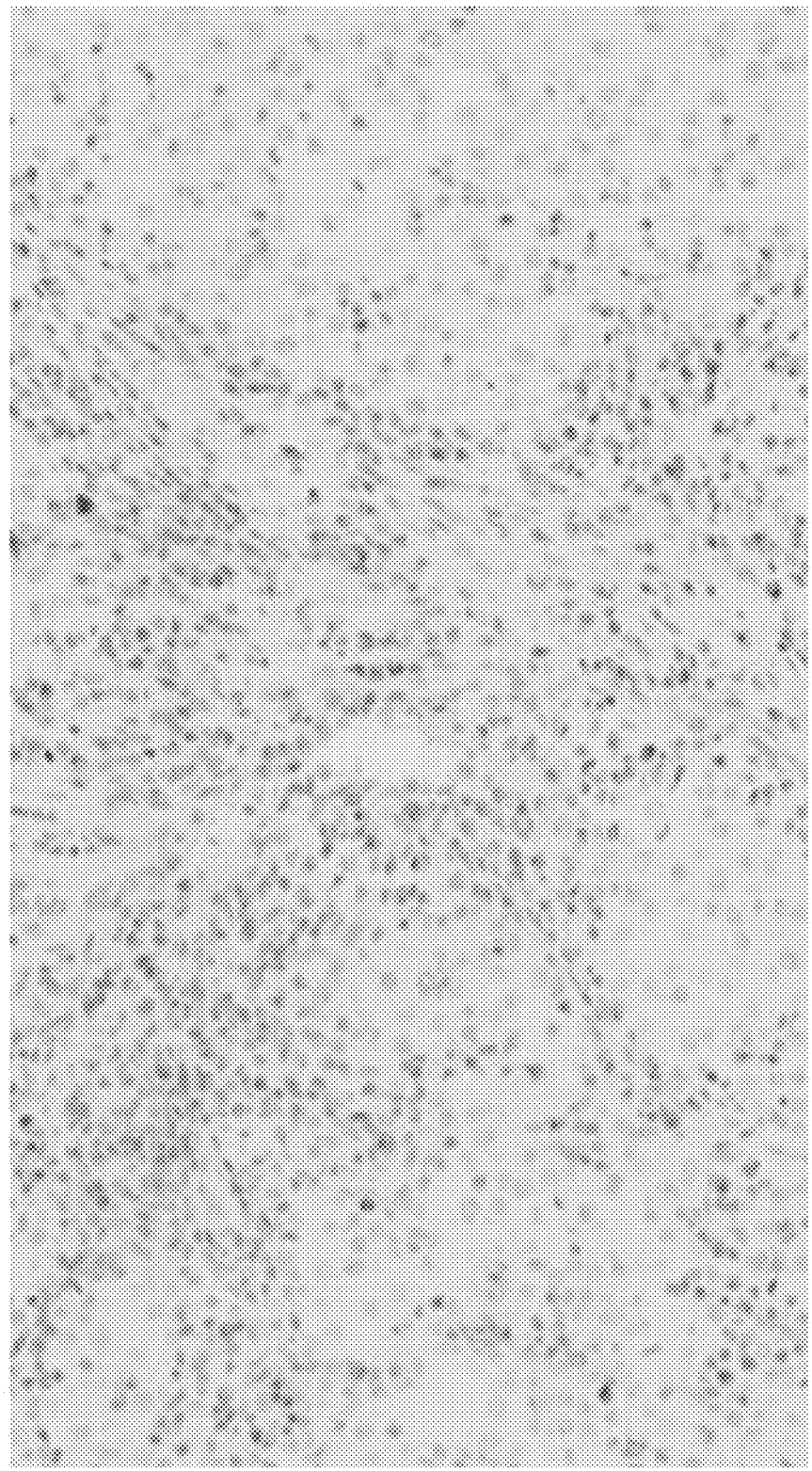
Figure 4B:
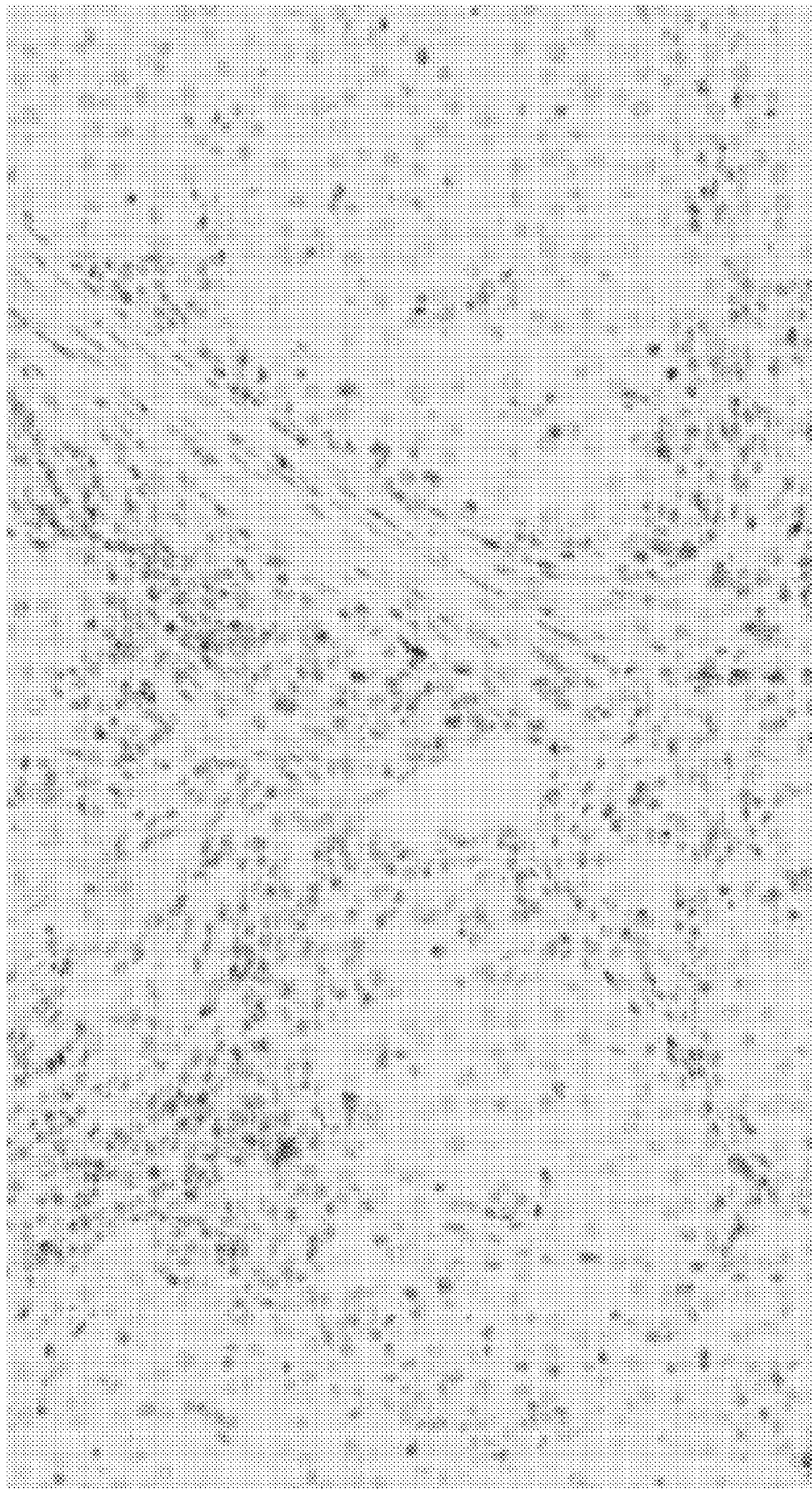
Figure 5A:
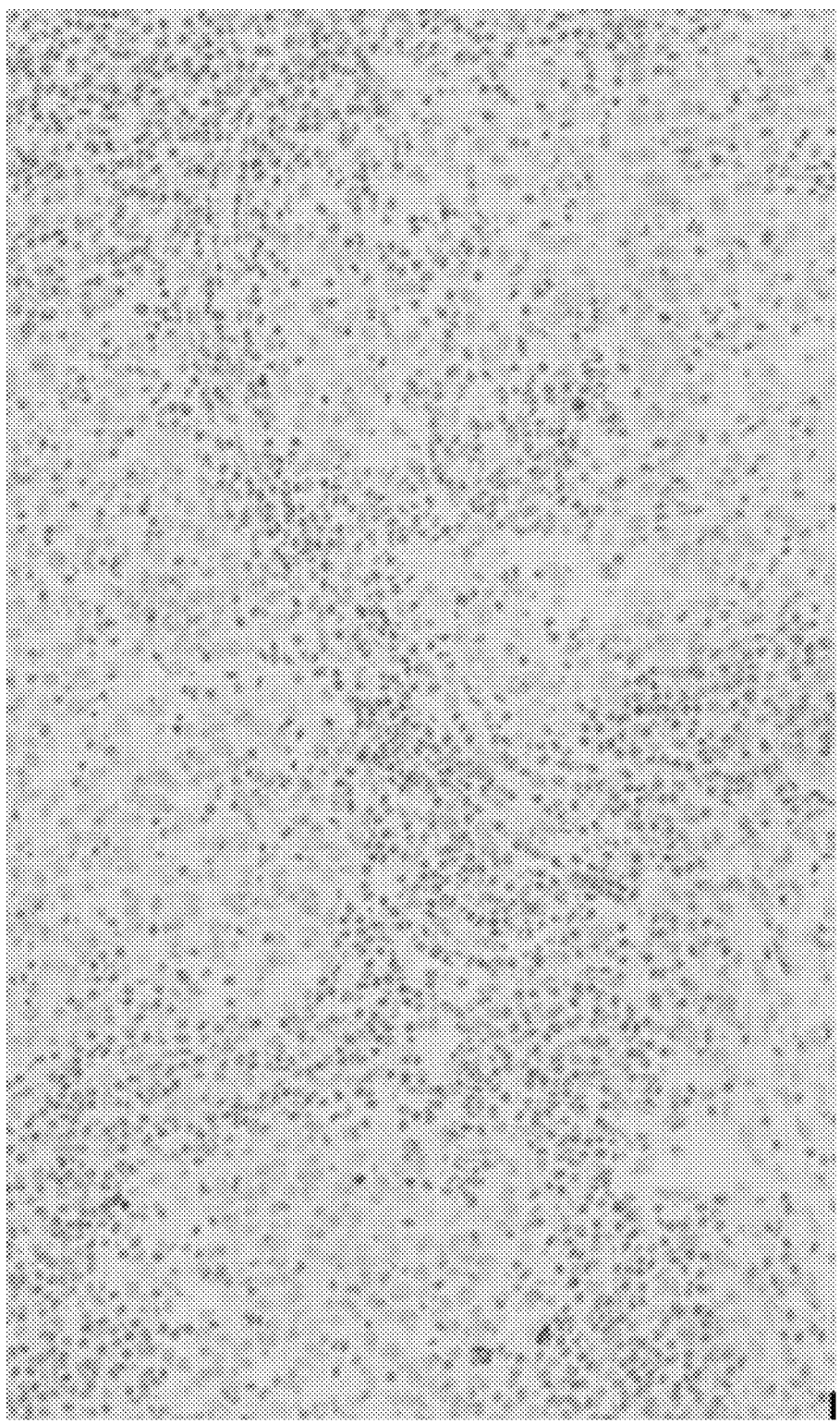
Figure 5B:
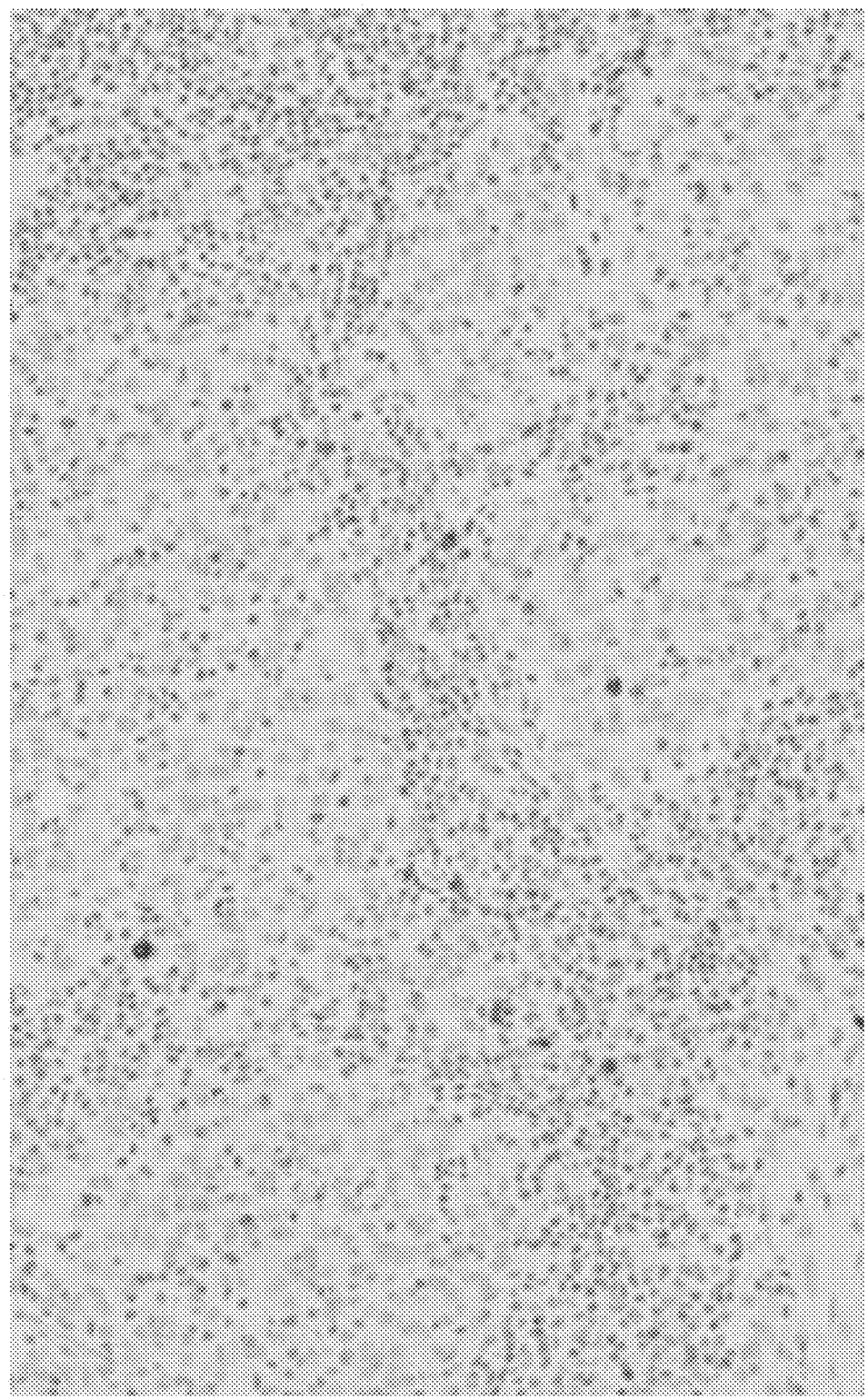
Figure 6A:
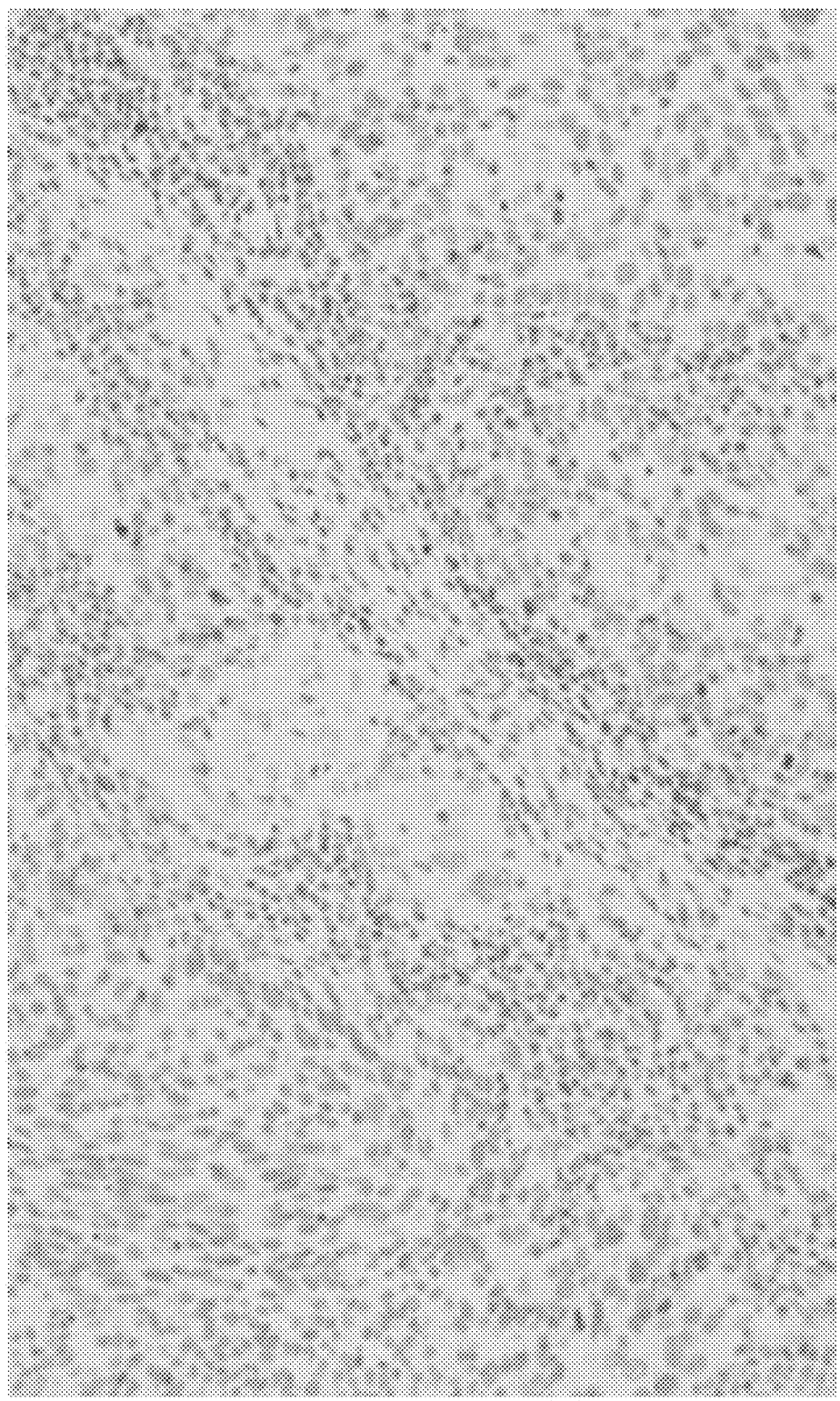
Figure 6B:
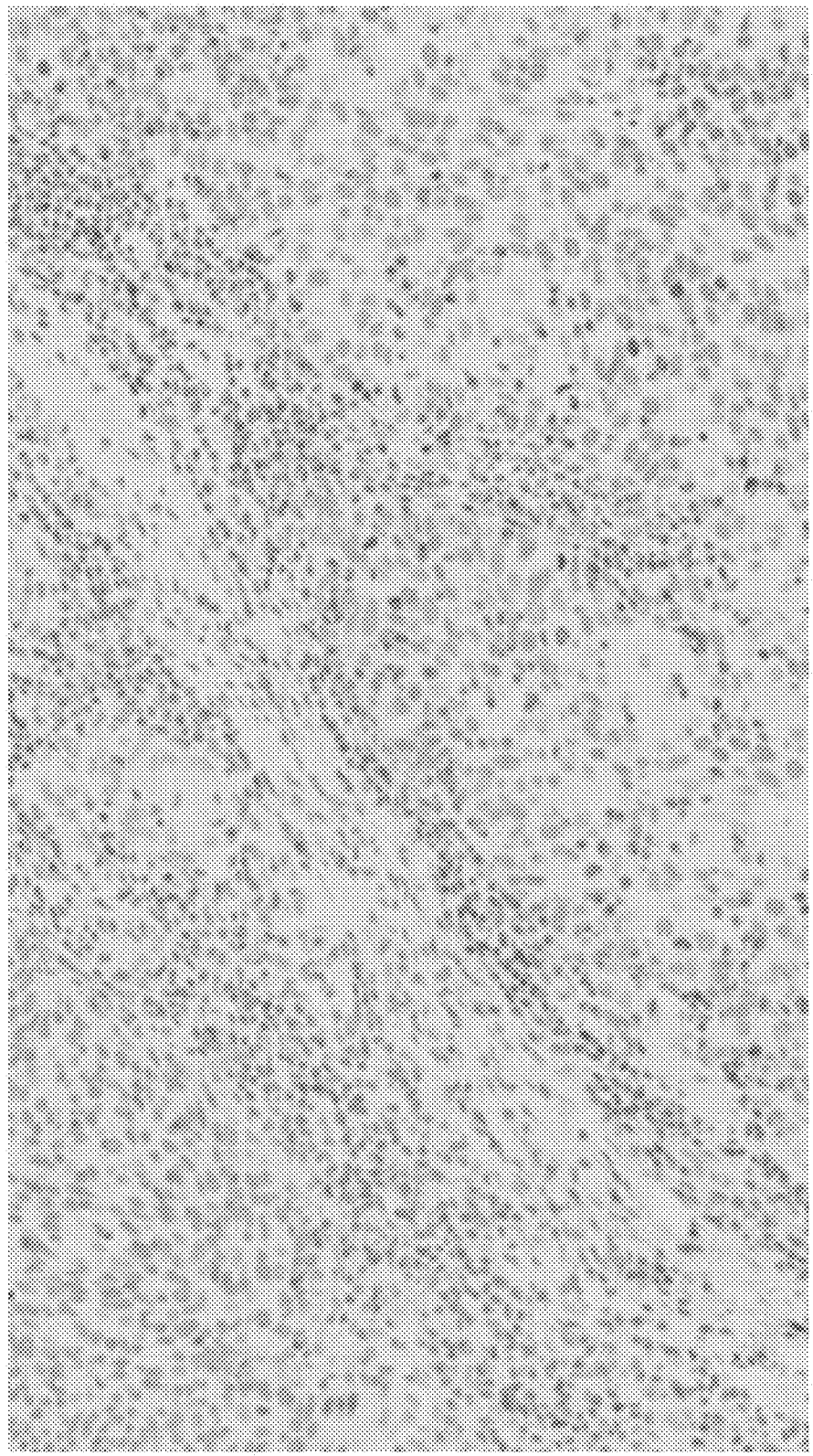
Figure 7A:
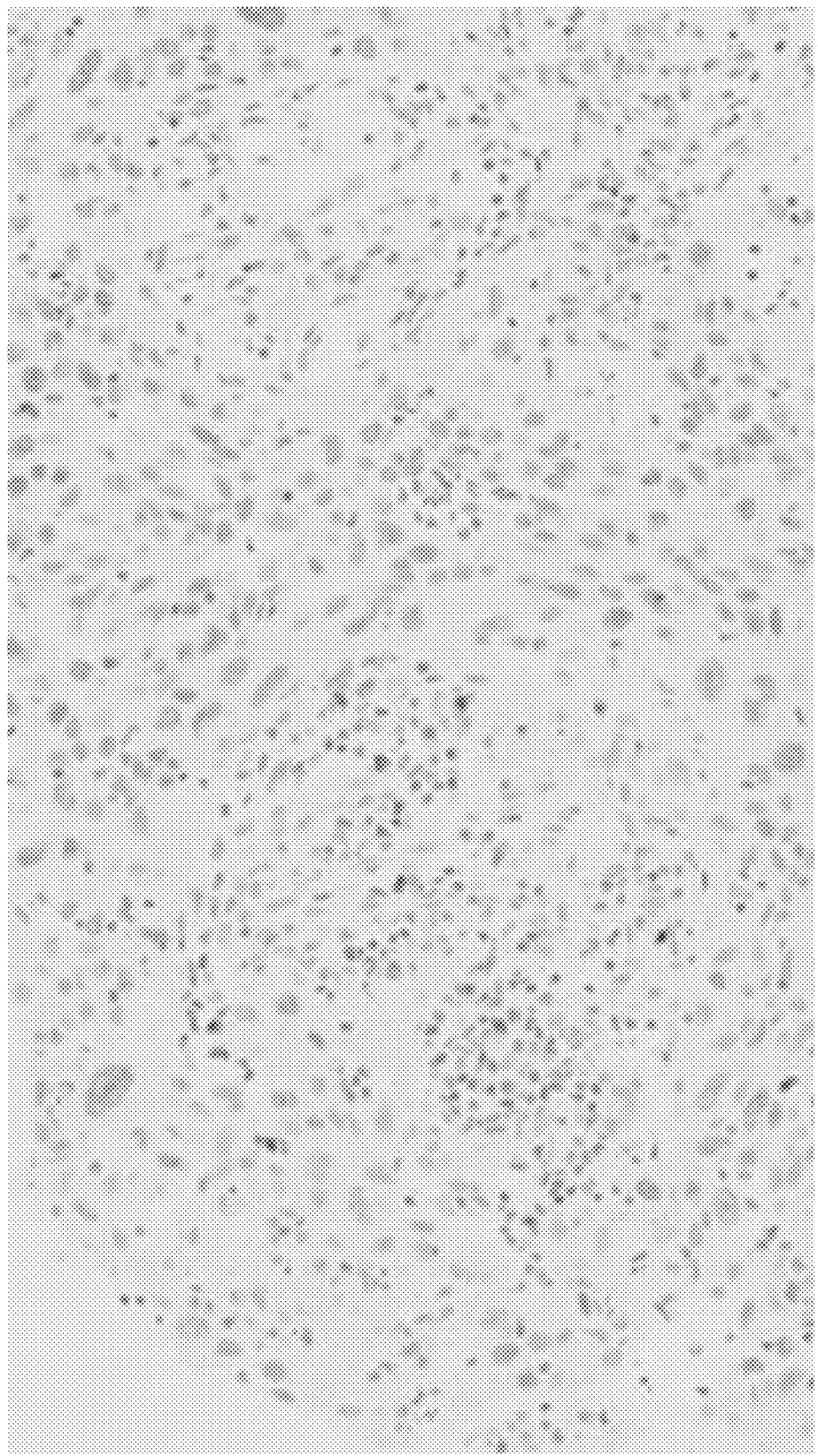
Figure 7B:
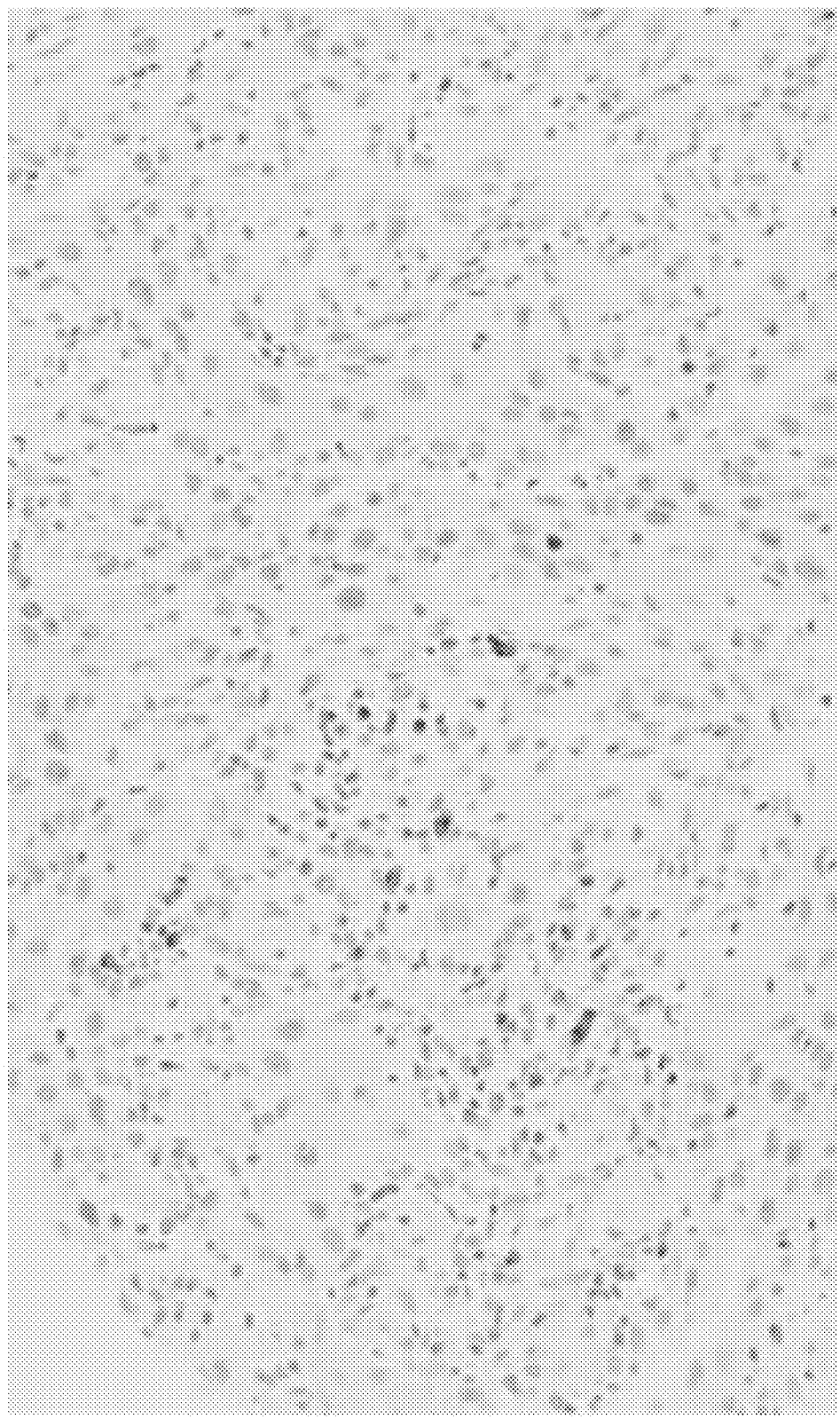
Figure 8A:
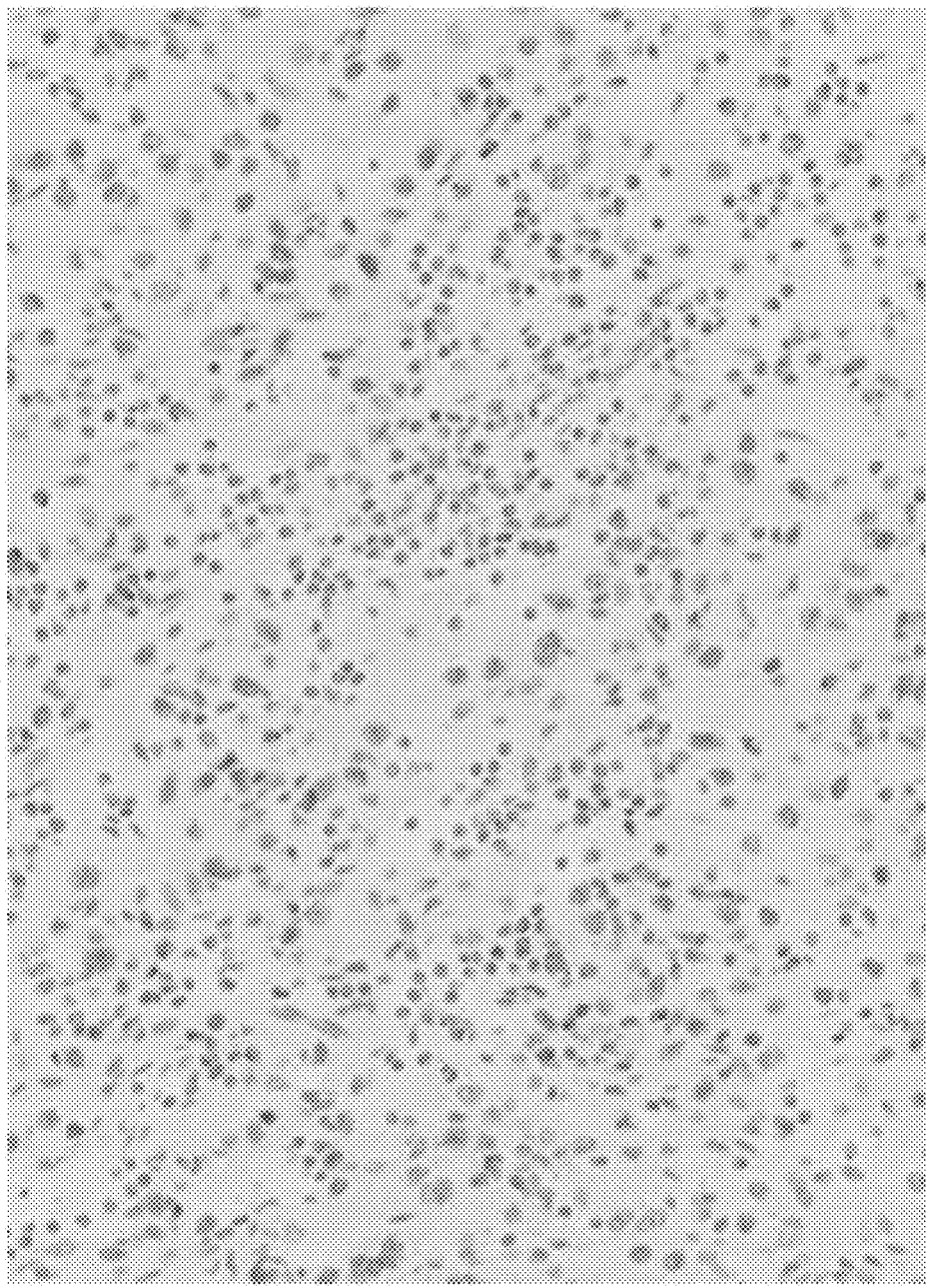
Figure 8B:
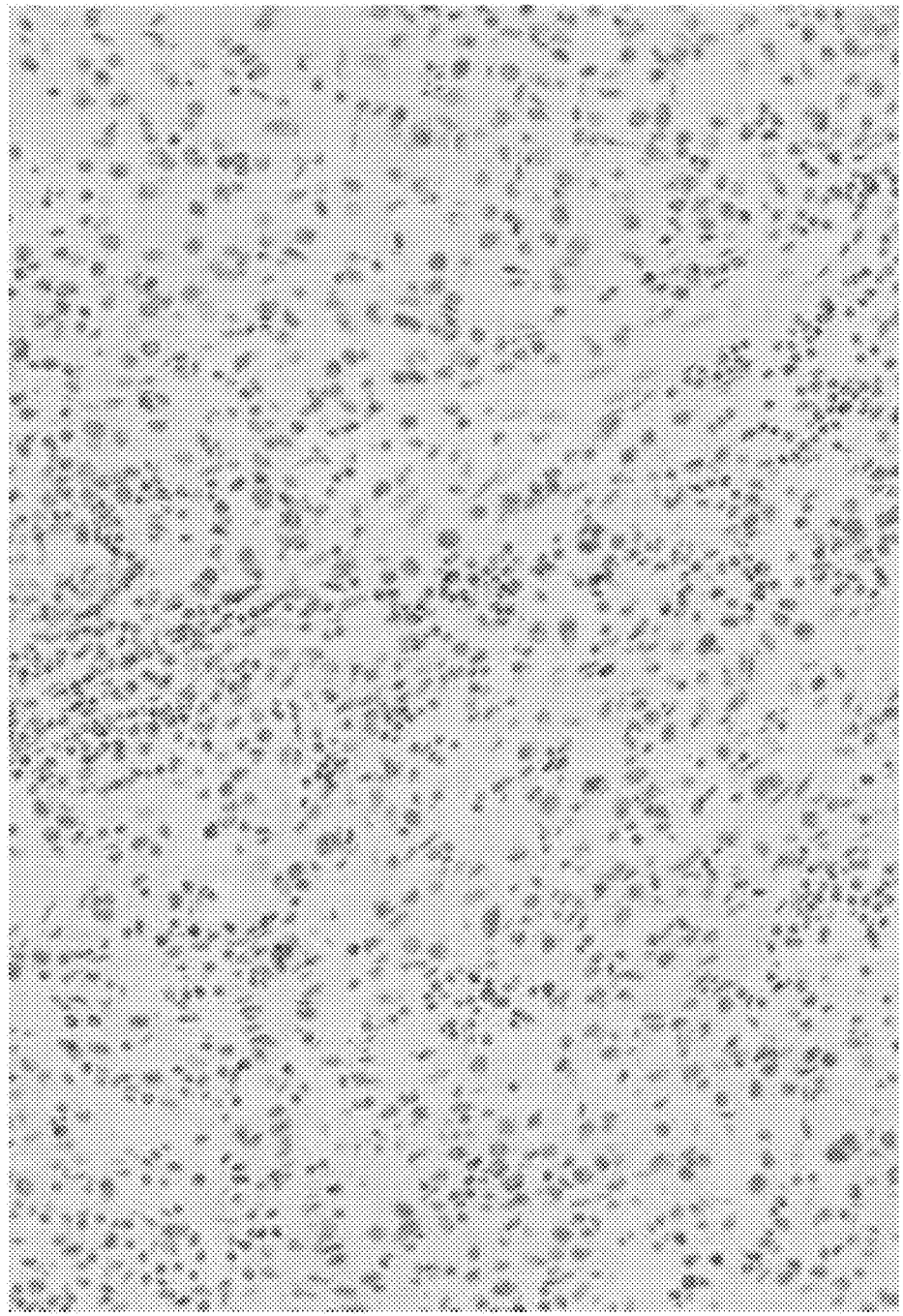

FIG. 2 illustrates an image of IHC staining on a renal cell carcinoma (RCC) using the standard visualization system EnVision FLEX+ with DAB chromogen (brown) and the exemplary clone 12H8. The image illustrates LAG-3 staining of activated T cells in an area of lymphocyte infiltration among the tumor cells (the Tumor Micro Environment (TME)); where the image shows that LAG-3 clone 12H8 does not stain the tumor cells and that the staining of activated T cells morphologically has three staining patterns: cytoplasmatic (1), membrane (2) and Golgi staining (3).

FIG. 3A-B, FIG. 4A-B, FIG. 5A-B, FIG. 6A-B, FIG. 7A-B and FIG. 8A-B illustrate IHC staining images of tumor tissue samples of malignant melanoma (FIG. 3A-B and FIG. 4A-B), lung NSCLC (FIG. 5A, FIG. 5B, FIG. 6A and FIG. 6B), lung adenocarcinoma (FIG. 7A and FIG. 7B) and renal cell carcinoma (RCC) (FIG. 8A and FIG. 8B) using the standard visualization system EnVision FLEX+ with DAB chromogen (brown) and: FIG. 3A, FIG. 4A, FIG. 5A, FIG. 6A, FIG. 7A and FIG. 8A showing a reference LAG-3 antibody clone 17B4 (Novus Bio), compared to the exemplary LAG-3 antibody clone 12H8 as shown in FIG. 3B, FIG. 4B, FIG. 5B, FIG. 6B, FIG. 7B and FIG. 8B); all images illustrate LAG-3 staining of activated T cells in areas of lymphocyte infiltration among the tumor cells within the TME; the images show that neither the reference LAG-3 antibody clone 17B4 nor the exemplary clone 12H3 stain the tumor cells and that the exemplary clone 12H8 matches or even exceed the reference clone 17B4 regarding specific staining intensity, lack of unwanted background staining and number of cells stained, when comparing figures A to figures B of the different tumor types.

Figure 9:
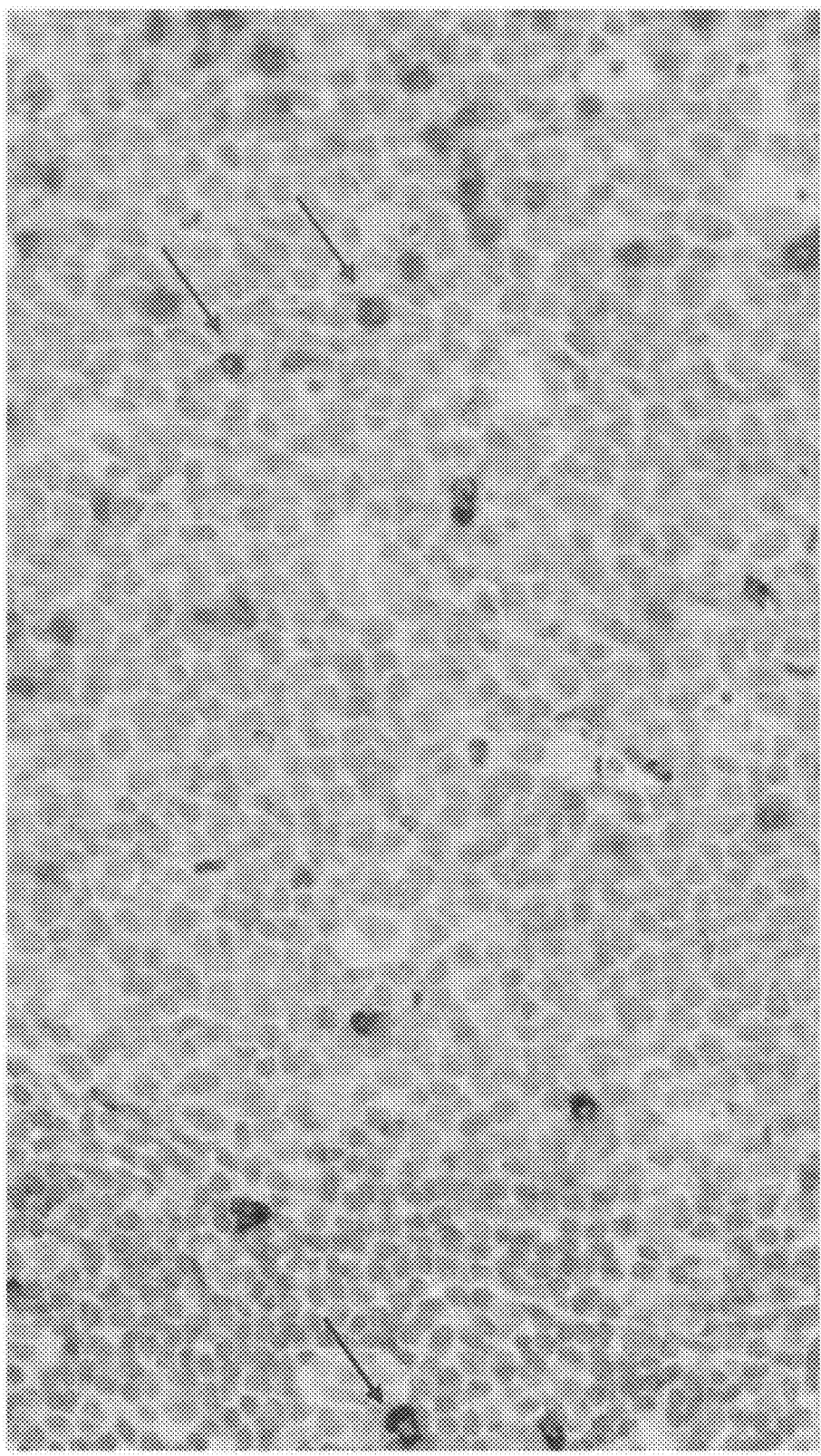
Figure 10:
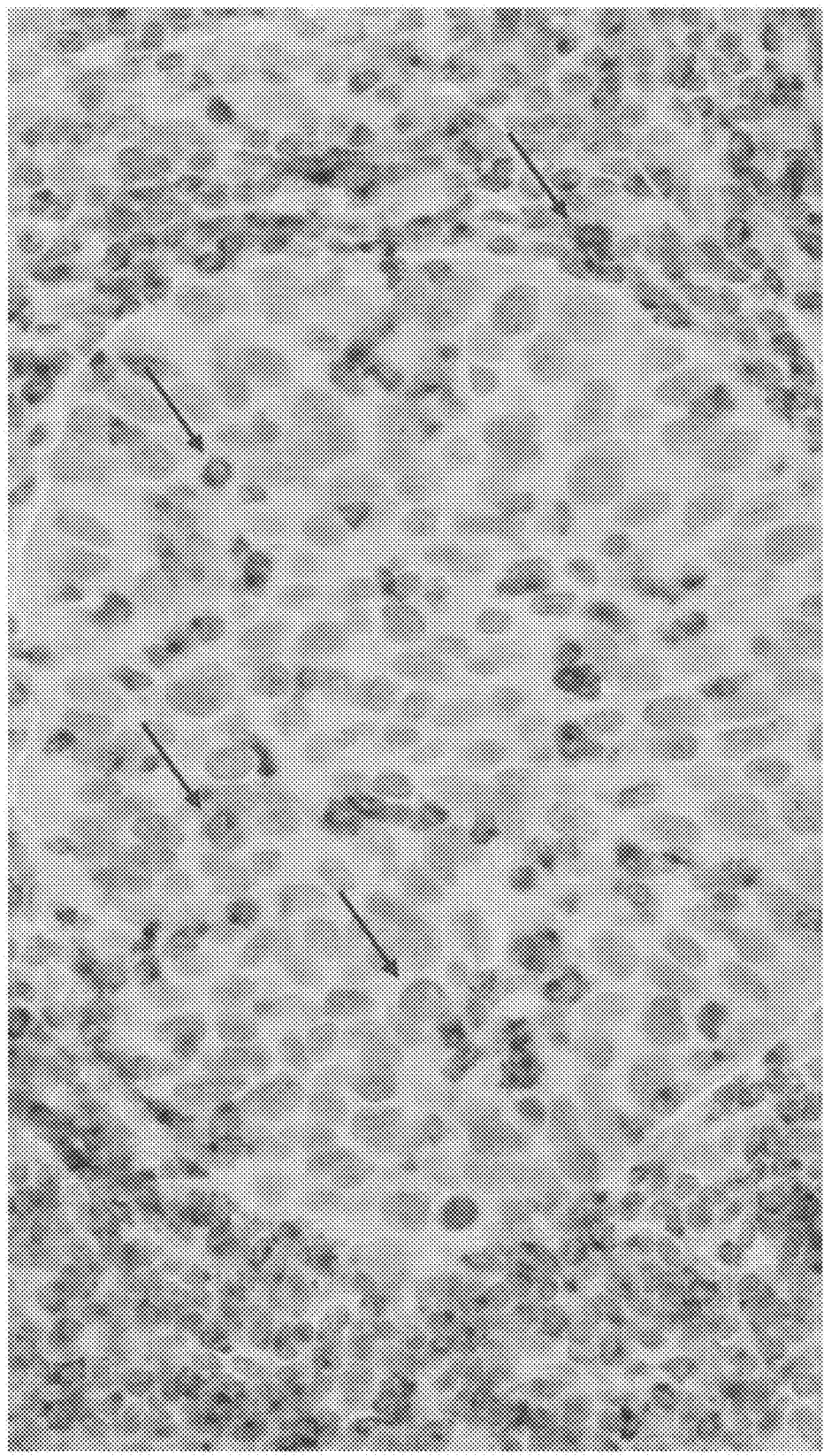
Figure 11:
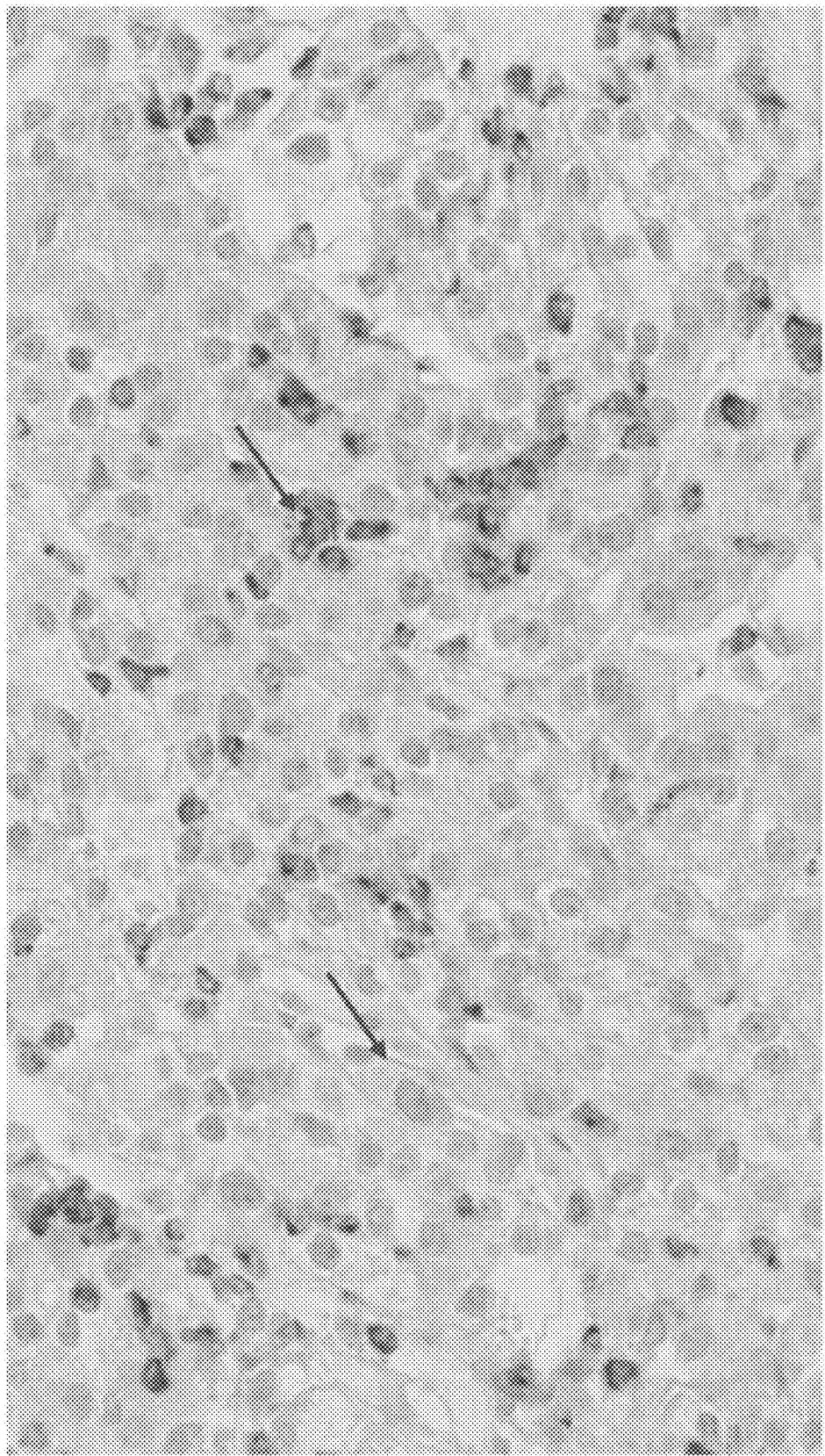

FIG. 9-11 illustrates double IHC staining of tissue samples of normal tonsil:

FIG. 9 illustrates tumor tissue samples of Lung Squamous cell Carcinoma (SQC) (FIG. 10) and kidney renal cell carcinoma (RCC) (FIG. 11); the double IHC staining method follows the protocol of Petersen, et al. 2018 [18] using the EnVision FLEX+™ system in a sequential manner, where the exemplary LAG-3 antibody, clone 12H8 (HRP DAB chromagen) constitutes the first layer followed by a sulfuric acid block step and adding an extra EnVision FLEX+™ staining layer on top with PD1 antibody, clone NAT105 (magenta chromogen)); and FIG. 9 illustrates that LAG-3 is co-localized with the PD1 T cell marker in a subpopulation of activated T cells in the germinal center of the tonsil. Other cells belonging to the activated T cell population is only stained by PD1. The B lymphocytes in the germinal center are negative for both the LAG-3 and the PD1 antibody, illustrating the specificity of both these antibodies: (Red arrow: strongly LAG-3 positive, DAB overshadows magenta PD1. Green arrow: weakly pos LAG-3 with both DAB membrane and DAB golgi and PD1 magenta stain visible). PD1 positive, LAG-3 negative T cells: (orange arrow).

FIG. 10 and FIG. 11 illustrate LAG-3 and PD1 double staining of: Lung Non-Small Cell Lung Cancer NSCLC (FIG. 10) and Renal Clear Cell Carcinoma (RCC) (FIG. 11), respectively, using the methodology described above: LAG-3 is co-localized with PD1 (T cell marker) in activated T cells within the Tumor Micro-Environment (TME) of both tumors; a few of these T cells are only positive for PD1, whereas all the squamous tumor cells in the lung and renal tumor clear cells are negative; these findings confirm the specificity of the exemplary LAG-3 antibody, clone 12H8; for FIG. 10 and FIG. 11: (Red arrow: LAG-3 co-localized with PD1 in activated T cells within the Tumor Micro Environment (TME); orange arrow: LAG-3 negative/PD1 positive T cell; in FIG. 10: blue arrow: Squamous tumor cells negative for LAG-3 and PD1; in FIG. 11, Blue arrow: RCC tumor cell negative for LAG-3 and PD1).

Figure 12:
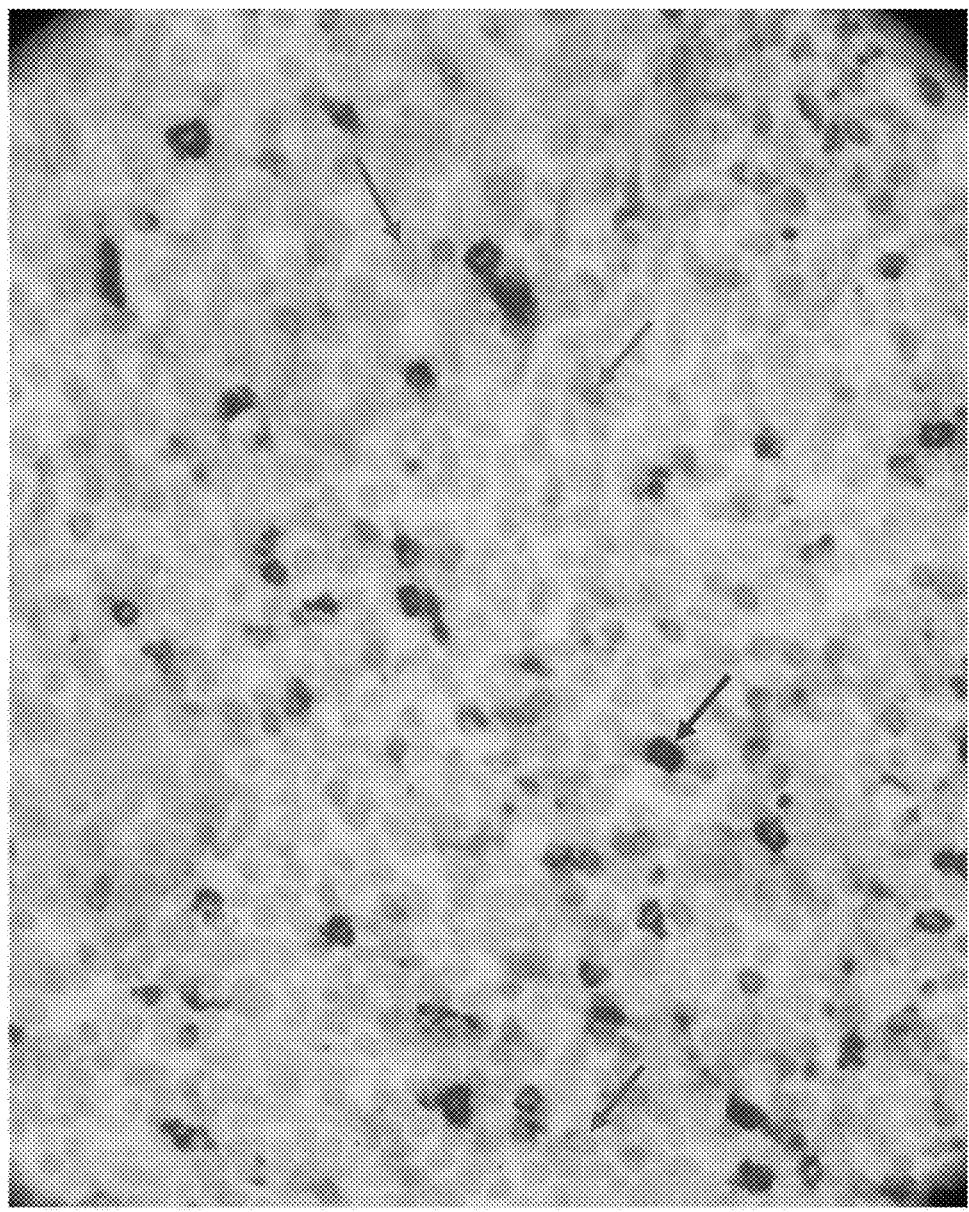
Figure 13:
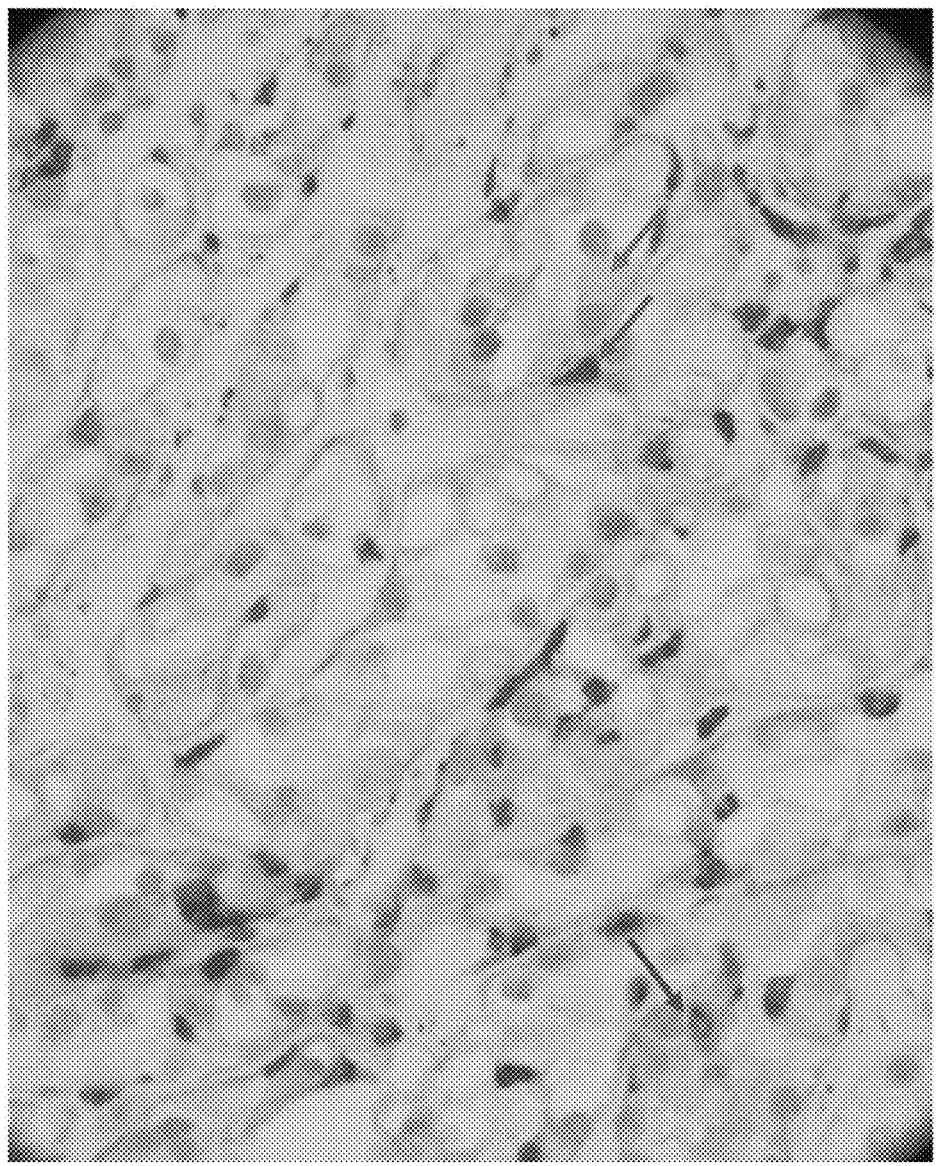
Figure 14:
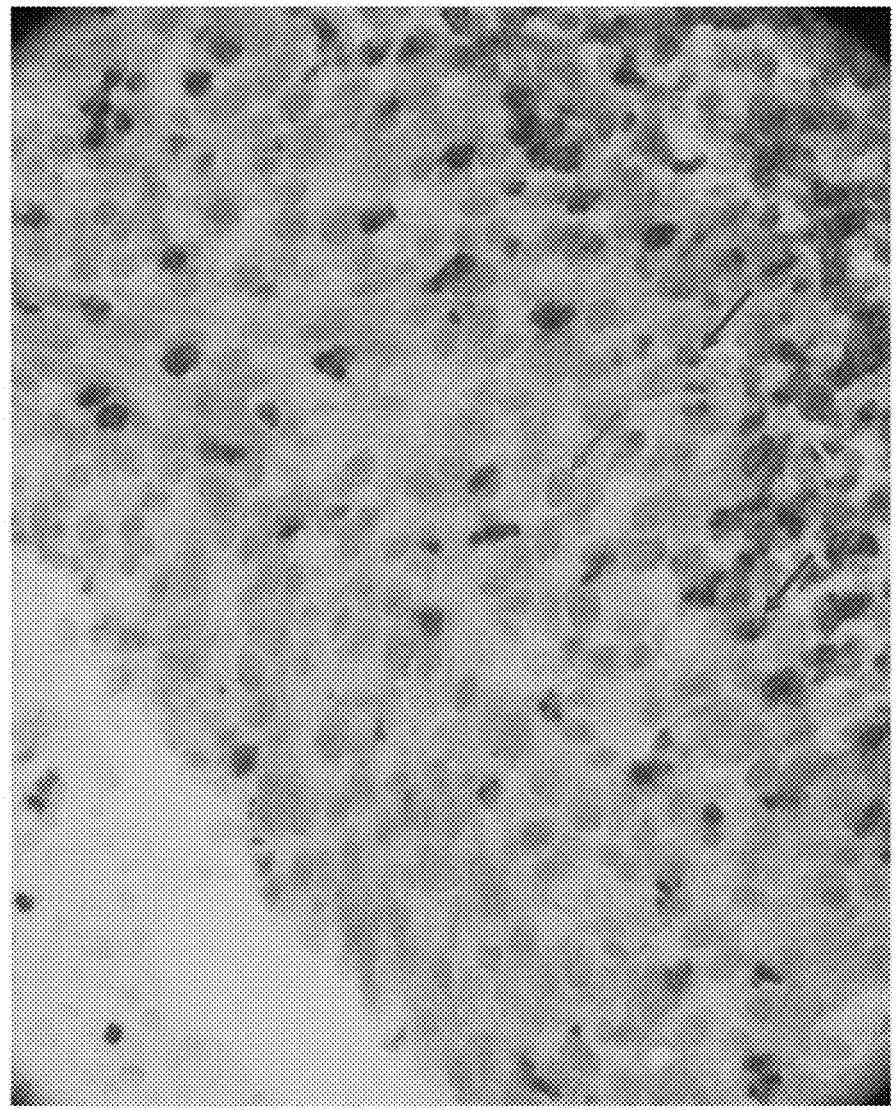

FIG. 12, FIG. 13 and FIG. 14 illustrate triple IHC staining of normal tonsil (FIG. 12), tumor tissue samples of Lung Squamous cell Carcinoma (SQC) (FIG. 13) and kidney Renal Cell Carcinoma (RCC) (FIG. 14); the triple IHC staining utilizes a super sensitive system with the above mentioned sulfuric acid blocking step between the three layers of antibodies: the exemplary LAG-3 antibody, clone 12H8 (HRP DAB chromgen), polyclonal (Dako GA503) CD3 antibody (HRP magenta chromogen), CK-pan antibody, clone AE1/AE1 (yellow substrate); and FIG. 12 illustrates that LAG-3 is co-localized with CD3 T cell marker in a subpopulation of activated T cells in the area of the tonsil below the tonsil crypt epithelia and in T cells migrating through the epithelia; many T cells only express the CD3 marker, consistent with LAG-3 only being expressed in activated T cells; many other B lymphocytes in the area are not stained with neither LAG-3 nor CD3; the CK pan antibody stain the epithelial cells and none of the lymphocytes; the image illustrates the localization of the LAG-3 positive T cells and the co-localization with CD3 T cell marker confirm the specificity of the LAG-3 antibody: (red arrow: strongly LAG-3 positive, DAB overshadows magenta CD3; green arrow: weakly positive LAG-3 with both DAB membrane and DAB golgi and CD3 magenta stain visible); CD3 positive, LAG-3 negative T cells: (orange arrow); epithelial cells positive for CK-pan and negative for LAG-3 (blue arrow).

FIG. 13 and FIG. 14 illustrates the co-localization of LAG-3 and CD3 T cell marker in a subpopulation of the T cells among the tumor infiltrating lymphocytes in TME in the kidney RCC tumor and the lung SQC tumor. A few T cells only express CD3 and all the renal tumor cells and the lung tumor cells is only stained with the CK pan antibody, confirming visually that the exemplary LAG-3 antibody is restricted to a subpopulation of T cells and is not expressed on tumor cells; red arrow indicates: activated T-cells in the TME, double positive for LAG-3 and CD3; blue arrow: RCC tumor (FIG. 13) and Squamous tumor (FIG. 14) cells only positive for CK pan; green arrow: activated LAG-3 and CD3 double positive T-cells surrounding tumor cells; orange arrow: T cells negative for LAG-3 and positive for CD3

Like reference symbols in the various drawings indicate like elements.

DETAILED DESCRIPTION

In alternative embodiments, provided are chimeric or a recombinant antibodies (Ab), or antigen binding fragments thereof, or monomeric or dimeric antigen binding proteins, that can specifically bind to human LAG-3 polypeptides, including human LAG-3 polypeptides expressed on the surface of lymphocytes such as activated T cells that have infiltrated tumors, or human LAG-3 polypeptides expressed on tumor infiltrating lymphocytes (TILs). In alternative embodiments, provided are products of manufacture and kits comprising the chimeric or a recombinant Abs, or antigen binding fragments thereof, or monomeric or dimeric antigen binding proteins, as provided herein, or nucleic acids encoding them, and methods for making and using them. In alternative embodiments, chimeric or a recombinant antibodies (Ab), or antigen binding fragments thereof, or monomeric or dimeric antigen binding proteins as provided herein are used for in vitro diagnostics, for example, by immunohistochemistry (IHC), for example, in IHC protocols to diagnose, detect and/or treat a cancer, for example bladder cancer, urothelial carcinoma, a breast cancer or a mammary carcinoma or a ductal carcinoma in situ (DCIS), a carcinoid, Hodgkin's Lymphoma, chronic lymphocytic leukemia, colorectal cancer, ovarian cancer, a lung cancer, a Non-Small Cell Lung Cancer (NSCLC), a kidney cancer or renal cell carcinoma or a renal carcinoma, a Renal Clear cell Carcinoma (RCC), mesothelioma or a malignant pleural mesothelioma, a squamous cell carcinoma, an anal squamous cell carcinoma, pancreatic cancer, and a melanoma or a malignant melanoma, by their ability to specifically bind to activated T cells that have infiltrated a tumor, for example, including tumor infiltrating lymphocytes (TILs). Thus, the chimeric or a recombinant antibodies (Ab), or antigen binding fragments thereof, or monomeric or dimeric antigen binding proteins as provided herein can be used as a companion diagnostic for the diagnosis and treatment of cancer by specifically staining TILs.

Expression of Recombinant Chimeric Antibodies

In alternative embodiments, chimeric and/or recombinant antibodies (Abs), the antigen binding fragments thereof, or the monomeric or dimeric antigen binding proteins as provided herein, including the exemplary chimeric or recombinant anti-human LAG-3 Abs comprising heavy chain variable region SEQ ID NO:2 and light chain variable region SEQ ID NO:3, with or without a signal peptide, can be expressed as a recombinant Ab using, for example, a plasmid or any expression vehicle encoding the respective heavy and light chains, or the heavy chain and the light chain can be encoded in separate expression vehicles.

In some embodiments, the heavy and light chains can be (cis- or trans-) expressed from any plasmid, cosmid, recombinant virus or equivalent vector, for example, from a pTT5™ vector(s) (National Research Council Canada, NRC-CNRC, Canada) or equivalents.

In alternative embodiments, the expression vehicles (such as a plasmid) containing exemplary Ab-encoding nucleic acid(s) as provided herein are expressed in in vitro expression systems or are expressed in cultured tissues, cells or organoids, which can be a bacterial, fungal, mammalian, yeast, insect or plant cell expression systems, or hybrid or synthetic expression system. For example, exemplary Ab-encoding nucleic acid(s) can be expressed in a human embryonic kidney (HEK) cell such as an HEK293-6E cell. In alternative embodiment, the vector or vectors expressing exemplary Ab-encoding nucleic acid(s), for example, exemplary heavy and/or light chains, are episomal or are chromosomally integrated, for example, in a stable cell line capable of synthesizing, optionally inducibly synthesizing, the heavy and/or light chains.

In alternative embodiments, provided are nucleic acids encoding chimeric or recombinant Abs as provided herein. Nucleic acids as provided herein can be made, isolated and/or manipulated by, for example, cloning and expression of cDNA libraries, amplification of message or genomic DNA by PCR, and the like. Nucleic acids used to practice embodiments as provided herein, whether RNA, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, fungal, mammalian, yeast, insect or plant cell expression systems, or hybrid or synthetic expression systems.

Alternatively, these nucleic acids can be synthesized in vitro by well-known chemical synthesis techniques, as described in, for example, Martin et al, ACS Synth. Biol. (2017) 6, 7, 1370-1379; Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids, such as, for example, subcloning, labeling probes (for example, random-primer labeling using Klenow polymerase, nick translation, amplification), sequencing, hybridization and the like are well described in the scientific and patent literature, see, for example, Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice embodiments as provided herein comprises screening and re-cloning inserts isolated or amplified from, for example, genomic clones or cDNA clones. Sources of nucleic acids include recombinant nucleic acid sequences, genomic or cDNA libraries contained and/or expressed in, for example, mammalian artificial chromosomes (MACs), see, for example, U.S. Pat. Nos. 5,721,118; 6,025,155; human artificial chromosomes, see, for example, Rosenfeld (1997) Nat. Genet. 15:333-335; yeast artificial chromosomes (YAC); bacterial artificial chromosomes (BAC); P1 artificial chromosomes, see, for example, Woon (1998) Genomics 50:306-316; P1-derived vectors (PACs), see, for example, Kern (1997) Biotechniques 23:120-124; cosmids, recombinant viruses, phages or plasmids.

In alternative embodiments, nucleic acids as provided herein are operably linked to transcriptional regulatory elements, including promoters, with can be constitutive or inducible transcriptional regulatory elements.

In alternative aspects, provided are "expression cassettes" comprising a nucleotide sequence as provided herein, for example encoding a chimeric or recombinant antibody as provided herein. Expression cassettes can include at least a transcriptional regulatory element, for example, a promoter, operably linked with an antibody coding sequence, and optionally can also include transcription termination signals. Additional factors necessary or helpful in effecting expression may also be used, for example, enhancers.

In alternative aspects, expression cassettes used to practice embodiments as provided herein include plasmids, expression vectors, recombinant viruses, any form of recombinant "naked DNA" vector, and the like. In alternative aspects, a "vector" used to practice embodiments as provided herein can comprise a nucleic acid that can infect, transfect, transiently or permanently transduce a cell. In alternative aspects, a vector used to practice embodiments as provided herein can be a naked nucleic acid, or a nucleic acid complexed with protein or lipid. In alternative aspects, vectors used to practice embodiments as provided herein can comprise viral or bacterial nucleic acids and/or proteins, and/or membranes (for example, a cell membrane, a viral lipid envelope, etc.). In alternative aspects, vectors used to practice embodiments as provided herein can include, but are not limited to replicons (for example, RNA replicons, bacteriophages) to which fragments of DNA may be attached and become replicated. Vectors thus include, but are not limited to RNA, autonomous self-replicating circular or linear DNA or RNA (for example, plasmids, viruses, and the like, see, for example, U.S. Pat. No. 5,217,879), and can include both the expression and non-expression plasmids. In alternative aspects, the vector used to practice embodiments as provided herein can be stably replicated by the cells during mitosis as an autonomous structure, or can be incorporated within the host's genome.

In alternative aspects, "promoters" used to practice embodiments as provided herein include all sequences capable of driving transcription of a coding sequence in a cell, for example, a bacterial, yeast, fungal, plant, insect (for example, baculovirus) or mammalian cell. Thus, promoters used in the constructs include cis-acting transcriptional control elements and regulatory sequences that are involved in regulating or modulating the timing and/or rate of transcription of a gene. For example, a promoter used to practice embodiments as provided herein can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences can interact with proteins or other biomolecules to carry out (turn on/off, regulate, modulate, etc.) transcription.

"Constitutive" promoters used to practice embodiments as provided herein can be those that drive expression continuously under most environmental conditions and states of development or cell differentiation. "Inducible" or "regulatable" promoters used to practice embodiments as provided herein can direct expression of a nucleic acid as provided herein under the influence of environmental conditions or developmental conditions. Examples of environmental conditions that may affect transcription by inducible promoters used to practice embodiments as provided herein include the presence of an inducing factor administered to a cell.

In alternative embodiments, antibodies used to practice embodiments as provided herein can comprise any "mimetic" and/or "peptidomimetic" form. In alternative embodiments, peptides and polypeptides used to practice embodiments as provided herein can comprise synthetic chemical compounds which have substantially the same structural and/or functional characteristics of the natural polypeptide, for example, a chimeric or recombinant antibody as provided herein. The mimetic used to practice embodiments as provided herein can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. Routine experimentation will determine whether a mimetic is effective for practicing the invention, for example, if a mimetic composition is effective in specifically binding a human LAG-3 protein. Methodologies detailed herein and others known to persons skilled in the art may be used to select or guide one to choose effective mimetic for practicing the compositions and/or methods as provided herein.

Polypeptide mimetic compositions for practicing embodiments as provided herein can comprise any combination of non-natural structural components. In alternative aspects, mimetic compositions for practicing embodiments as provided herein can comprise one or all of the following three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, for example, a beta turn, gamma turn, beta sheet, alpha helix conformation, and the like. For example, a polypeptide can be characterized as a mimetic when all or some of its residues are joined by chemical means other than natural peptide bonds.

Purification and Isolation of Recombinant Proteins

In alternative embodiments, chimeric or the recombinant antibodies, antigen binding fragments thereof, or monomeric or dimeric antigen binding proteins, are substantially purified or isolated, and optionally the substantially purified or isolated forms are the forms used in immunohistochemistry methodologies and/or as reagents, kits and/or products of manufacture as provided herein.

In alternative embodiments, chimeric or the recombinant antibodies, antigen binding fragments thereof, or monomeric or dimeric antigen binding proteins, are substantially purified or isolated using: physicochemical fractionation, for example, using differential precipitation, size-exclusion or solid-phase binding of immunoglobulins based on size, charge or other shared chemical characteristics of antibodies in typical samples; class-specific affinity, for example, solid-phase binding of particular antibody classes (for example, IgG or IgM) by immobilized biological ligands (for example, proteins, lectins, and the like) that have specific affinity to immunoglobulins, and this can purify all antibodies of the target class without regard to antigen specificity; or antigen-specific affinity, for example, affinity purification of only those antibodies in a sample that bind to a particular antigen molecule through their specific antigen-binding domains, where this purifies all antibodies that bind the antigen without regard to antibody class or isotype.

In alternative embodiments, chimeric or the recombinant antibodies, antigen binding fragments thereof, or monomeric or dimeric antigen binding proteins, are substantially purified or isolated using standard isolation methodologies such as chromatography, for example, Ion Exchange (IEX) Chromatography, Hydrophobic Interaction Chromatography (HIC), countercurrent chromatography, immunoaffinity and/or size exclusion chromatography.

In alternative embodiments, chimeric or the recombinant antibodies, antigen binding fragments thereof, or monomeric or dimeric antigen binding proteins, are generated in bioreactors, for example, a perfusion bioreactor, using continuous expression and purification processes, for example, as described by Vogg et al Methods Mol Biol. 2018; vol 1850:147-178, or using stirred-tank or rocking bioreactor systems, followed by purification.

Products of Manufacture and Kits

Provided are products of manufacture and kits comprising chimeric or recombinant anti-human LAG-3 Abs as provided, and for practicing methods as provided herein using the chimeric or recombinant anti-human LAG-3 Abs as provided herein; and optionally the products of manufacture and kits can further comprise some or all reagents needed to perform an IHC, and optionally can comprise instructions for practicing methods as provided herein.

In alternative embodiments, products of manufacture have attached thereto or affixed (optionally covalently bound) on or onto chimeric or a recombinant antibodies (Ab), or antigen binding fragments thereof, or monomeric or dimeric antigen binding proteins as provided herein, and optionally products of manufacture as provided herein are or comprise arrays, biochips, slides, trays, dishes (for example, microtiter dishes), phages or phagemids.

Immunohistochemistry

In alternative embodiments, immunohistochemistry methodologies and/or reagents used to practice compositions, products of manufacture, kits or methods as provided herein can include or comprise or comprise use of any IHC protocol, IHC armamentarium, device and/or image or data analysis system, for practicing IHC or IHC reagents known in the art, for example, as described in U.S. Pat. No. 10,565,479 (describing methods for identifying blurred areas in digital images of stained tissue); U.S. Pat. No. 10,564,076 (describing systems for analytical (or IHC) sample preparation); U.S. Pat. No. 10,551,395 (describing an automated histological staining system); U.S. Pat. No. 10,551,378 (describing a tissue staining method); U.S. Pat. No. 10,504,224 (describing a digital tissue image analysis system for IHC); U.S. Pat. No. 10,501,777 (describing simultaneous, multiplexed detection and quantification of protein expression in IHC); U.S. Pat. No. 10,488,340 (describing method for extracting an image of a target fluorophore in a biological material); U.S. Pat. No. 10,453,195 (describing methods of detecting tissue areas of interest using digital pathology imaging); U.S. Pat. No. 10,438,381 (describing devices, systems and methods for generating a digital image of a tissue section); U.S. Pat. No. 10,416,176 (describing methods for processing specimens in an automated histological staining system); U.S. Pat. No. 10,393,633 (describing methods for processing and inhibiting the degradation of an IHC sample); U.S. Pat. No. 10,217,011 (describing handling of IHC slides); U.S. Pat. No. 10,209,165 (describing automated or semi-automated methods for assessing the quality of staining of a specimen containing cells); U.S. Pat. No. 10,126,216 (describing methods for fixing tissue samples for IHC); U.S. Pat. No. 9,423,322.

In alternative embodiments, chimeric or the recombinant antibodies, antigen binding fragments thereof, or monomeric or dimeric antigen binding proteins, in IHC protocols, or kits, as provided herein are substantially purified or isolated or are in the form of an unpurified or partially purified culture supernatant.

In alternative embodiments, methods as provided herein can use or comprise reagents for detecting or visualizing an antibody-antigen interaction using any products or methods know in the art, for example, and IHC protocol or reagents.

In alternative embodiments, methods as provided herein comprise use of chromogenic immunohistochemistry (CIH), wherein a primary antibody (for example, chimeric or a recombinant antibodies (Ab), or antigen binding fragments thereof, or monomeric or dimeric antigen binding proteins as provided herein) or secondary antibody (for example, where the secondary antibody binds to (the primary antibody) chimeric or a recombinant antibodies (Ab), or antigen binding fragments thereof, or monomeric or dimeric antigen binding proteins as provided herein after they have specifically bound to, paired with, associated with, or configured with a LAG-3 epitope or polypeptide) is conjugated to an enzyme, such as peroxidase (or immunoperoxidase), for example, a horseradish peroxidase (HRP), that can catalyze a color-producing reaction.

In alternative embodiments, methods as provided herein comprise use of immunofluorescence, where a primary or a secondary antibody is tagged to a fluorophore, such as fluorescein or fluorescein isothiocyanate (FITC), a triarylmethane dye such as rhodamine or rhodamine derivatives (for example, tetramethylrhodamine (TRITC), rhodamine 6G, rhodamine 123, rhodamine B, carboxytetramethylrhodamine (TAMRA), tetramethylrhodamine (TMR), sulforhodamine 101), aminomethylcoumarin acetate (AMCA), ALEXA™ or DYLIGHT™ fluors. 3,3'-Diaminobenzidine (DAB) also can be used.

In alternative embodiments, methods as provided herein comprise use of a direct method or one-step staining method where a primary antibody (for example, chimeric or a recombinant antibodies (Ab), or antigen binding fragments thereof, or monomeric or dimeric antigen binding proteins as provided herein) is labeled and reacts directly with an antigen, for example, in a tissue sections. While this technique utilizes only one antibody and therefore is simple and rapid, the sensitivity may be lower due to little signal amplification.

In alternative embodiments, methods as provided herein comprise use of an indirect method where an unlabeled primary antibody (first layer) binds to a target antigen (LAG-3), for example, in a tissue or organ, and a labeled secondary antibody (second layer) then is reacted with the primary antibody. The secondary antibody can be against the isotype, for example, IgG, of the animal species in which the primary antibody is derived. This method can be more sensitive than direct detection strategies because of signal amplification due to the binding of several secondary antibodies to each primary antibody if the secondary antibody is conjugated to a detecting agent such as a fluorescent or enzyme reporter.

In alternative embodiments, further amplification is achieved if the secondary antibody is conjugated to several detecting molecules, for example, biotin molecules, which can recruit complexes of avidin-, streptavidin- or NEUTRAVIDIN™ protein-bound enzyme.

In alternative embodiments, the IHC is performed on tissue sections or tissue biopsies, for example, paraformaldehyde (PFA) fixed tissues or organs, or formalin-fixed paraffin-embedded tissues. In alternative embodiments, a tissue is sliced or used whole. Before sectioning, the tissue sample can be embedded in a medium, for example, paraffin wax or cryomedia. Tissue sections can be sliced on a variety of instruments, most commonly using a microtome, cryostat, or vibratome. Specimens can be sliced at a range of about 3 µm to 5 µm. The slices can be mounted on slides, dehydrated using alcohol washes of increasing concentrations (for example, 50%, 75%, 90%, 95%, 100%), and cleared using a detergent like xylene before being imaged under a microscope.

Depending on the method of fixation and tissue preservation, the sample may require additional steps to make the LAG-3 epitopes available for antibody binding, including deparaffinization and antigen retrieval. For formalin-fixed paraffin-embedded tissues, antigen-retrieval is often necessary, and can comprise pre-treating the sections with heat or proteases.

In alternative embodiments, the IHC is performed using an ENVISION DUOFLEX DOUBLESTAIN SYSTEM™ (EnVision DuoFLEX Doublestain System) (Agilent, San Jose, Calif.), which allows for staining of two or more markers on a single slide. In alternative embodiments, the IHC is performed using an EnVision FLEX HRP Magenta, High pH (Dako Omnis) system, and binding can be visualized by EnVision FLEX HRP Magenta Chromogen. In alternative embodiments, the IHC is performed using EnVision FLEX Mini Kit, High pH, which is a high-sensitivity visualization system intended for use in IHC together with Dako AUTOSTAINER™ instruments; his dual link system detects primary mouse and rabbit antibodies and the reaction is visualized by 3,3'-Diaminobenzidine (DAB) chromogen (DAB forms a water-insoluble brown precipitate when oxidized, for example, by a peroxidase).

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Development of Exemplary Anti-LAG Antibodies

This example describes the development of an exemplary anti-LAG antibody as provided herein.

An antigen used to immunize rabbits was a synthetic peptide sequence, GPPAAAPGHPLAPGPHPAAPSS-WGPRPRR (SEQ ID NO:1), representing the amino acids 70-98 of human LAG-3. The peptide was conjugated to KLH and used for immunizations of 5 rabbits.

The rabbits' antibody titers were tested against the peptide, and the bleeds were tested in IHC for LAG-3 specific staining in IHC. All 5 rabbits showed LAG-3 specific staining in IHC.

B-cell selection was performed with one rabbit resulting in several promising B-cell clones producing antibody specific against LAG-3. Cloning of antibody coding sequences were performed into an expression plasmid.

Sequence of rabbit anti-human LAG-3 antibody, clone 12H8, heavy chain variable region is:

```
                                            (SEQ ID NO: 2)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSS
```

Sequence of rabbit anti-human LAG-3 antibody, clone 12H8, light chain variable region is:

```
                                            (SEQ ID NO: 3)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVK
```

Recombinant antibody was produced and tested in standard IHC showing LAG-3 specific staining. This antibody was further tested to confirm specificity against LAG-3.

Expression of recombinant antibody was performed using HEK293-6E cell line and pTT5 based vectors. This transient expression of antibody takes around 10 days after transfection and is a fast and high yield method compared to hybridoma technology.

Other methods can be used for the transient transfection and making a stable cell line for the expression of antibody. For example, in one embodiment, adihydrofolate reductase (DHFR)-deficient cell line CHO DG44 cells is used (for example, using the FREEDOM™ DG44 kit (Gibco)).

Creation of a stable cells line requires selection and cloning of the cells to generate a good expressing and stable cell line. It is important that the generated stable cell line is monoclonal to ensure production of homogenous monoclonal antibody. Other cells lines can be used both for transient and/or stable transfection.

LAG-3 Antibody Clone Development

For the development of anti-human LAG-3 antibody different antigens were designed and produced. The antigen used for the final clone, 12H8, was a synthetic peptide, covering the amino acids 70 to 98;

```
                                            (SEQ ID NO: 1)
        GPPAAAPGHPLAPGPHPAAPSSWGPRPRR.
```

This sequence is part of the extracellular domain of human LAG-3 protein and makes an extra loop compared to CD4 which has high structural homology to LAG-3 which has previously been used for raising LAG-3 antibodies [19].

Rabbits were immunized and the titer tested by ELISA. Subsequently specificity testing was performed using serum sample for IHC of tissue array containing different tissues: Normal tonsils, reactive lymph nodes, malignant melanoma (clinical tissue), normal liver, carcinoid tumor, mamma carcinoma, colon carcinoma, cerebellum, normal prostate, normal kidney and normal pancreas. All of the rabbit serum showed some degree of specificity against LAG-3 protein in IHC. The rabbit producing the best performing serum sample was chosen for B-cell selection. Blood sample was taken from the rabbit and subjected to B-cell selection, isolating the B-cells producing antibodies binding the LAG-3 antigen. The B-cells were cultured monoclonally under stimulating conditions, and the resulting cell culture supernatant was tested in ELISA to identify wells containing B-cells producing antigen binding antibodies. ELISA positive cell culture supernatants were further tested in super sensitive IHC, identifying cell culture supernatants having antibodies specific for LAG-3 in IHC. 10 clones were identified showing LAG-3 specific staining in IHC.

The two best IHC performing B-cell clones were chosen for cloning. The selection and prioritizing of B-cell clones were performed using a super sensitive IHC on both normal and tumor tissues, as listed above. The tissues were selected by IHC screening with a reference LAG-3 antibody (clone 17B4 Novus bio), choosing both normal and tumor tissues with high expression of LAG-3. All the B-cell clones were then compared to the LAG-3 reference antibody in the super sensitive IHC. Clones with the correct specificity, correct morphological expression (membrane, cytoplasmatic and golgi) and the best sensitivity (signal to noise ratio) were chosen and prioritized.

The cultured cells of the respective wells of the two clones were lysed, and the RNA extracted and used for production of cDNA. The variable heavy and light chains, respectively, were amplified by PCR, using custom made primers and the PCR product was cloned into custom made expression vector (using pTT5 backbone) containing the respective rabbit constant heavy and light IgG chains, yielding functional antibody coding sequences. Heavy and light chains plasmids were transfected into HEK293-6E cell line and recombinant antibody was produced and tested in standard IHC (Envision FLEX) protocol.

Antibody clone 12H8 showed nice crisp and specific performance in IHC, with the correct morphological expression (both membrane, cytoplasmatic and golgi). The sensitivity was excellent, both in high expression tissue (tonsil) and low expression tissue (melanoma). FIG. 1 illustrates an image of staining a tonsil using super sensitive IHC using a cell culture supernatant of the exemplary clone 12H8.

Furthermore, this clone had no adverse staining in any of the other included tissues (liver, colon adenocarcinoma, mamma carcinoma, carcinoid, normal colon, cerebellum, prostate, kidney and pancreas), nor any unspecific background staining.

The recombinant monoclonal rabbit anti human LAG-3 antibody was subsequently subjected to further testing. A 6 point titration using the IHC system EnVision FLEX (Agilent) was performed on the above mentioned tissue array supplemented with additional three clinical tissues (Non Small Cell Lung Cancer (NSCLC), Renal Clear cell Carcinoma (RCC) and malignant melanoma. A preliminary optimal concentration was obtained, matching the tissue localization, the morphological expression, the strength of the staining and the best signal to noise ratio on both normal tissue and tumor tissue with the reference antibody. The optimal version of this exemplary protocol was determined as:

LAG-3 Exemplary IHC Protocol with LAG-3 Clone:

Optimal antibody concentration 1.75 ug/mL in 53022 antibody dilution buffer. Target retrieval in High pH TR buffer. Visualization system: EnVision FLEX+ with Rabbit Linker.

As a confirmation of the optimal protocol, the LAG-3 antibody was tested on a small tissue package consisting of seven positive clinical tissues (2× lung NSCLC, 1× lung adenocarcinoma, 2× malignant melanoma, 2× kidney RCC) and two negative clinical tissues (1× lung carcinoma, 1× melanoma).

LAG-3 Multiplexing

LAG-3 blocking is under several clinical investigations, many using LAG-3 in combination with other targets. Among these are PD-1. Exemplary LAG-3 antibodies as provided herein were tested in double to show the degree of colocalization with PD-1, and CD3, respectively, as illustrated in FIG. 9-11, as discussed above.

LAG-3 Expression on Tumor Infiltrating Lymphocytes (TILs)

In clinical tissues LAG-3 is expressed on subpopulations of Tumor Infiltrating Lymphocytes (TILs) and not on tumor cells ([32], as shown in FIG. 12-14, as discussed above.

Sequencing Data

Sequencing data for the exemplary anti-human LAG-3 antibody, clone 12H8:

Heavy Chain Variable Region (SEQ ID NO: 2)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSS

CDR regions are underlined. CDR1 amino acid (aa) residues 25-32, CDR2 aa residues 50-56, CDR3 aa residues 95-101, of SEQ ID NO:2. CDR regions according to numbering by IMGT numbering (http://www.imgt.org/).

Light Chain Variable Region:

(SEQ ID NO: 3)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVK

CDR regions are underlined. CDR1 aa residues 27-34, CDR2 aa residues 52-54, CDR3 aa residues 91-102, of SEQ ID NO:3. CDR regions according to numbering by IMGT numbering (http://www.imgt.org/).

The disclosures of each of the following references is incorporated by reference herein in their entireties:

REFERENCES

1. Andrews, L. P., et al., LAG3 (CD223) as a cancer immunotherapy target. Immunol Rev, 2017. 276(1): p. 80-96.
2. Huard, B., et al., Cellular expression and tissue distribution of the human LAG-3-encoded protein, an MHC class II ligand. Immunogenetics, 1994. 39(3): p. 213-7.
3. Workman, C. J., et al., LAG-3 regulates plasmacytoid dendritic cell homeostasis. J Immunol, 2009. 182(4): p. 1885-91.
4. Hemon, P., et al., MHC class II engagement by its ligand LAG-3 (CD223) contributes to melanoma resistance to apoptosis. J Immunol, 2011. 186(9): p. 5173-83.
5. Gandhi, M. K., et al., Expression of LAG-3 by tumor-infiltrating lymphocytes is coincident with the suppression of latent membrane antigen-specific CD8+ T-cell function in Hodgkin lymphoma patients. Blood, 2006. 108(7): p. 2280-9.
6. Chen, J. and Z. Chen, The effect of immune microenvironment on the progression and prognosis of colorectal cancer. Med Oncol, 2014. 31(8): p. 82.
7. Matsuzaki, J., et al., Tumor-infiltrating NY-ESO-1-specific CD8+ T cells are negatively regulated by LAG-3 and PD-1 in human ovarian cancer. Proc Natl Acad Sci USA, 2010. 107(17): p. 7875-80.
8. Li, F. J., et al., Expression of LAG-3 is coincident with the impaired effector function of HBV-specific CD8(+) T cell in HCC patients. Immunol Lett, 2013. 150(1-2): p. 116-22.
9. Giraldo, N. A., et al., Orchestration and Prognostic Significance of Immune Checkpoints in the Microenvironment of Primary and Metastatic Renal Cell Cancer. Clin Cancer Res, 2015. 21(13): p. 3031-40.
10. Takaya, S., H. Saito, and M. Ikeguchi, Upregulation of Immune Checkpoint Molecules, PD-1 and LAG-3, on CD4+ and CD8+ T Cells after Gastric Cancer Surgery. Yonago Acta Med, 2015. 58(1): p. 39-44.
11. Yang, Z. Z., et al., Expression of LAG-3 defines exhaustion of intratumoral PD-1(+) T cells and correlates with poor outcome in follicular lymphoma. Oncotarget, 2017. 8(37): p. 61425-61439.
12. Norstrom, M. M., et al., Progression of benign prostatic hyperplasia is associated with pro-inflammatory mediators and chronic activation of prostate-infiltrating lymphocytes. Oncotarget, 2016. 7(17): p. 23581-93.
13. Deng, G., et al., BRAF mutation is frequently present in sporadic colorectal cancer with methylated hMLH1, but not in hereditary nonpolyposis colorectal cancer. Clin Cancer Res, 2004. 10(1 Pt 1): p. 191-5.
14. He, Y., et al., LAG-3 Protein Expression in Non-Small Cell Lung Cancer and Its Relationship with PD-1/PD-L1 and Tumor-Infiltrating Lymphocytes. J Thorac Oncol, 2017. 12(5): p. 814-823.
15. Marcq, E., et al., Abundant expression of TIM-3, LAG-3, PD-1 and PD-L1 as immunotherapy checkpoint targets in effusions of mesothelioma patients. Oncotarget, 2017. 8(52): p. 89722-89735.
16. Burugu, S., et al., LAG-3+ tumor infiltrating lymphocytes in breast cancer: clinical correlates and association with PD-1/PD-L1+ tumors. Ann Oncol, 2017. 28(12): p. 2977-2984.
17. Yanik, E. L., et al., Association of HIV Status With Local Immune Response to Anal Squamous Cell Carcinoma: Implications for Immunotherapy. JAMA Oncol, 2017. 3(7): p. 974-978.
18. Meng, Q., et al., Expansion of Tumor-reactive T Cells From Patients With Pancreatic Cancer. J Immunother, 2016. 39(2): p. 81-9.
19. Woo, S. R., et al., Immune inhibitory molecules LAG-3 and PD-1 synergistically regulate T-cell function to promote tumoral immune escape. Cancer Res, 2012. 72(4): p. 917-27.
20. Huang, R. Y., et al., LAG3 and PD1 co-inhibitory molecules collaborate to limit CD8+ T cell signaling and dampen antitumor immunity in a murine ovarian cancer model. Oncotarget, 2015. 6(29): p. 27359-77.
21. Petersen, K. H., J. Lohse, and L. Ramsgaard, Automated sequential chromogenic IHC double staining with two HRP substrates. PLoS One, 2018. 13(11): p. e0207867.
22. Baixeras, E., et al., Characterization of the lymphocyte activation gene 3-encoded protein. A new ligand for human leukocyte antigen class II antigens. J Exp Med, 1992. 176(2): p. 327-37.

A number of embodiments of the invention have been described. Nevertheless, it can be understood that various modifications may be made without departing from the spirit and scope of the invention. Accordingly, other embodiments are within the scope of the following claims.

---

What is claimed is:

1. A chimeric or a recombinant antibody (Ab) or an antigen binding fragment thereof capable of specifically binding to a human Lymphocyte-Activation Gene 3 (LAG-3) polypeptide, comprising:
a heavy chain variable region comprising:
the three CDR1, CDR2 and CDR3 complementarity determining regions (CDRs) of SEQ ID NO:2, or CDR1 amino acid (aa) residues 25-32, CDR2 aa residues 50-56, and CDR3 aa residues 95-101, of SEQ ID NO:2; and
a light chain variable region comprising:
the three CDR1, CDR2 and CDR3 complementarity determining regions (CDRs) of SEQ ID NO:3, or CDR1 amino acid (aa) residues 27-34, CDR2 aa residues 52-54, and CDR3 aa residues 91-102, of SEQ ID NO:3.

2. The chimeric or recombinant antibody (Ab) or antigen binding fragment thereof of claim 1, fabricated as or in the form of:
an antigen-binding fragment,
a F(ab')$_2$,
a Fab',
a single-chain variable fragment (scFv),
a (scFv)$_2$,
a minibody, or
a diabody or a tetrabody.

3. The chimeric or recombinant antibody (Ab) or antigen binding fragment thereof of claim 1, wherein
the sequence of the heavy chain variable region consists of:

(SEQ ID NO: 2)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSS, and
the sequence of the light chain variable region consists of:

(SEQ ID NO: 3)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVK.

4. The chimeric or recombinant antibody (Ab) or antigen binding fragment thereof of claim 1, consisting of:
(a) a heavy chain variable region comprising the three CDR1, CDR2 and CDR3 complementarity determining regions (CDRs) of SEQ ID NO:2, or CDR1 amino acid (aa) residues 25-32, CDR2 aa residues 50-56, and CDR3 aa residues 95-101, of SEQ ID NO:2; and
(b) a light chain variable region comprising the three CDR1, CDR2 and CDR3 complementarity determining regions (CDRs) of SEQ ID NO:3, or CDR1 amino acid (aa) residues 27-34, CDR2 aa residues 52-54, and CDR3 aa residues 91-102, of SEQ ID NO:3.

5. The chimeric or recombinant antibody (Ab) or antigen binding fragment thereof of claim 1, comprising:
(a) a heavy chain variable region comprising:

(SEQ ID NO:2)
QSVKESEGGLFKPTDTLTLTCTVSGIDLSSGILVWVRQAPGSGLEWIGG

IDANGRAYYASWAKSRSTITRNTNENTVTLKMTSLTAADTATYFCAGGA

WNIWGPGTLVTVSS and
(b) a light chain variable region comprising:
AQVLTQTPSPVSAAVGGTVTIKCQSSQSVYDSNT-LAWFQQKPGQPPKLLMYSAST LAFGVPSRFSGSGS-GTQFTLTISDLECADAATYYCLGSYDCSSVDCT-AFGGGTEVV VK (SEQ ID NO:3).

6. The chimeric or recombinant antibody (Ab) or antigen binding fragment thereof of claim 1, wherein the antibody heavy chain is an IgM, IgG, IgA or IgE isotype heavy chain, and/or the light chain is a kappa or a lambda light chain.

7. The chimeric or recombinant antibody (Ab) or antigen binding fragment thereof of claim 1, comprising:
a light chain constant region comprising:

(SEQ ID NO: 4)
GDPGAPTVLIFPPAADQVATGTVTIVCVANKYFPDVTVTWEVDGTTQTTGI

ENSKTPQNSADCTYNLSSTLTLTSTQYNSHKEYTCKVTQGTTSVVQSFNRG

DC, or (SEQ ID NO: 5)
GDPVAPTVLIFPPAADQVATGTVTIVCVANKYFPDVTVTWEVDGTTQTTGI

ENSKTPQNSADCTYNLSSTLTLTSTQYNSHKEYTCKVTQGTTSVVQSFNRG

DC.

8. The chimeric or recombinant antibody (Ab) or antigen binding fragment thereof of claim 1, comprising:
(a) a light chain constant region comprising SEQ ID NO:4 or SEQ ID NO:5 having at least one, two, three, four, five, six, seven, eight, nine, ten, eleven or twelve or more conservative amino acid substitutions: or
(b) a light chain constant region having at least 95% sequence identity to SEQ ID NO:4 or SEQ ID NO:5.

9. The chimeric or recombinant antibody (Ab) or antigen binding fragment thereof of claim 1, comprising a heavy chain constant region having a sequence:

(SEQ ID NO: 6)
GQPKAPSVFPLAPCCGDTPSSTVTLGCLVKGYLPEPVTVTWNSGTLTNGVR

TFPSVRQSSGLYSLSSVVSVTSSSQPVTCNVAHPATNTKVDKTVAPSTCSK

PTCPPPELLGGPSVFIFPPKPKDTLMISRTPEVTCVVVDVSQDDPEVQFTW

YINNEQVRTARPPLREQQFNSTIRVVSTLPIAHQDWLRGKEEKCKVHNKAL

PAPIEKTISKARGQPLEPKVYTMGPPREELSSRSVSLTCMINGFYPSDISV

EWEKNGKAEDNYKTTPAVLDSDGSYFLYSKLSVPTSEWQRGDVFTCSVMHE

ALHNHYTQKSISRSPGK.

10. The chimeric or recombinant antibody (Ab) or antigen binding fragment thereof of claim 1, comprising:
   (a) a heavy chain constant region comprises SEQ ID NO:6 having at least one, two, three, four, five, six, seven, eight, nine, ten, eleven or twelve or more conservative amino acid substitutions; or
   (b) the sequence of the heavy chain constant region has at least 95% sequence identity to SEQ ID NO:6.

11. The chimeric or recombinant antibody (Ab) or antigen binding fragment thereof of claim 1, comprising an antibody light chain having a sequence:

(SEQ ID NO: 7)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVKGDPGAPTVLIFPPAADQVATGTVTIVCVANKYFPDVTVTW

EVDGTTQTTGIENSKTPQNSADCTYNLSSTLTLTSTQYNSHKEYTCKVTQG

TTSVVQSFNRGDC,
or (SEQ ID NO: 8)
AQVLTQTPSPVSAAVGGTVTIKCQSSQSVYDSNTLAWFQQKPGQPPKLLMY

SASTLAFGVPSRFSGSGSGTQFTLTISDLECADAATYYCLGSYDCSSVDCT

AFGGGTEVVVKGDPVAPTVLIFPPAADQVATGTVTIVCVANKYFPDVTVTW

EVDGTTQTTGIENSKTPQNSADCTYNLSSTLTLTSTQYNSHKEYTCKVTQG

TTSVVQSFNRGDC.

12. The chimeric or recombinant antibody (Ab) or antigen binding fragment thereof of claim 1, comprising an antibody heavy chain having a sequence:

(SEQ ID NO: 9)
QSVKESEGGLFKPTDTLTLTCTVSGIDLSSGILVWVRQAPGSGLEWIGGID

ANGRAYYASWAKSRSTITRNTNENTVTLKMTSLTAADTATYFCAGGAWNIW

GPGTLVTVSSGQPKAPSVFPLAPCCGDTPSSTVTLGCLVKGYLPEPVTVTW

NSGTLTNGVRTFPSVRQSSGLYSLSSVVSVTSSSQPVTCNVAHPATNTKVD

KTVAPSTCSKPTCPPPELLGGPSVFIFPPKPKDTLMISRTPEVTCVVVDVS

QDDPEVQFTWYINNEQVRTARPPLREQQFNSTIRVVSTLPIAHQDWLRGKE

FKCKVHNKALPAPIEKTISKARGQPLEPKVYTMGPPREELSSRSVSLTCMI

NGFYPSDISVEWEKNGKAEDNYKTTPAVLDSDGSYFLYSKLSVPTSEWQRG

DVFTCSVMHEALHNHYTQKSISRSPGK.

13. The chimeric or recombinant antibody (Ab) or antigen binding fragment thereof of claim 1, wherein the chimeric or recombinant Ab comprises:

(a) a light chain as set forth in SEQ ID NO:7 paired with a heavy chain as set forth in SEQ ID NO: 9, wherein the chimeric or recombinant Ab is capable of selectively binding to a human LAG-3 polypeptide; or
(b) a light chain as set forth in SEQ ID NO:8 paired with a heavy chain as set forth in SEQ ID NO: 9, wherein the chimeric or recombinant Ab is capable of selectively binding to a human LAG-3 polypeptide.

14. The chimeric or recombinant antibody (Ab) or antigen binding fragment thereof of claim 13, wherein the chimeric or recombinant Ab comprises:
   a light chain as set forth in SEQ ID NO:7 paired with with a heavy chain as set forth in SEQ ID NO:9, wherein the chimeric or recombinant Ab is capable of selectively binding to a human LAG-3 polypeptide.

15. The chimeric or recombinant antibody (Ab) or antigen binding fragment thereof of claim 13, wherein the chimeric or recombinant Ab comprises:
   a light chain as set forth in SEQ ID NO:8 paired with a heavy chain as set forth in SEQ ID NO: 9, wherein the chimeric or recombinant Ab is capable of selectively binding to a human LAG-3 polypeptide.

16. The chimeric or recombinant antibody (Ab) or antigen binding fragment thereof of claim 1, conjugated to or linked with a detectable agent.

17. The chimeric or recombinant antibody (Ab) or antigen binding fragment thereof of claim 16, wherein the detectable agent comprises an enzyme.

18. The chimeric or recombinant antibody (Ab) or antigen binding fragment thereof of claim 17, wherein the enzyme is a peroxidase, an alkaline phosphatase, or a beta-galactosidase, and optionally the peroxidase is a horse radish peroxidase (HRP).

19. The chimeric or recombinant antibody (Ab) or antigen binding fragment thereof of claim 16, wherein the detectable agent comprises:
   a biotin, a fluorescent or chemiluminescent label, a fluorophore, a cyanine or sulfoindo-cyanine, nile red, rhodamine, perylene, fluorenyl, coumarin, 7-methoxycoumarin (Mca), dabcyl, [2-(4-nitro-2,1,3-benzoxadiazol-7-yl)aminoethyl]trimethylammonium (NBD), Nile blue, Tamra or tetramethylrhodamine (TMR), HRP MAGENTA™ chromogen (Dako Omnis, Agilent), boron-dipyrromethene (BODIPY), or derivatives thereof), a dye, a radioisotope, a quantum dot or photoluminescent aqueous nanocrystal, a hapten or an antibody binding epitope or domain.

20. A chimeric or recombinant antibody (Ab) or antigen binding fragment thereof, capable of specifically binding to a human Lymphocyte-Activation Gene 3 (LAG-3) polypeptide, comprising:
   a heavy chain variable region comprising:
      the three CDR1, CDR2 and CDR3 complementarity determining regions (CDRs) of SEQ ID NO:2, or CDR1 amino acid (aa) residues 25-32, CDR2 aa residues 50-56, and CDR3 aa residues 95-101, of SEQ ID NO:2; and
   a light chain variable region comprising:
      the three CDR1, CDR2 and CDR3 complementarity determining regions (CDRs) of SEQ ID NO:3, or CDR1 amino acid (aa) residues 27-34, CDR2 aa residues 52-54, and CDR3 aa residues 91-102, of SEQ ID NO:3
   and wherein:
   (a) the sequence of the heavy chain variable region comprises SEQ ID NO:2 having at least one, two, three, four, five, six, seven, eight, nine, ten, eleven or twelve conservative amino acid substitutions outside the three CDR1, CDR2 and CDR3 complementarity determining regions (CDRs);
(b) the sequence of the light chain variable region comprises SEQ ID NO:3 having at least one, two, three, four, five, six, seven, eight, nine, ten, eleven or twelve conservative amino acid substitutions outside the three CDR1, CDR2 and CDR3 complementarity determining regions (CDRs);
(c) the sequence of the heavy chain variable region outside the three CDR1, CDR2 and CDR3 complementarity determining regions (CDRs) has at least 95% sequence identity to SEQ ID NO:2;
(d) the sequence of the light chain variable region outside the three CDR1, CDR2 and CDR3 complementarity determining regions (CDRs) has at least 95% sequence identity to SEQ ID NO:3:
(e) the sequence of the heavy chain variable region and the amino acid sequence SEQ ID NO:2 outside the three CDR1, CDR2 and CDR3 complementarity determining regions (CDRs) have a Z score of from 2 to 8, of a Z score of at least 8, when aligned using distance matrix alignment; or
(f) the sequence of the light chain variable region and the amino acid sequence SEQ ID NO:3 outside the three CDR1, CDR2 and CDR3 complementarity determining regions (CDRs) have a Z score of from 2 to 8, of a Z score of at least 8, when aligned using distance matrix alignment.

21. A method for detecting the presence of a human LAG-3 protein in a cell, a tissue, an organ or a portion of any of the foregoing, comprising:
    contacting the cell, tissue or organ or portion of any of the foregoing with a chimeric or recombinant antibody (Ab) or antigen binding fragment thereof of claim 1.

22. A method for diagnosing a LAG-3 protein-expressing cancer, or a cancer tissue having contained therein a LAG-3 expressing lymphocyte or a LAG-3 expressing tumor infiltrating lymphocyte (TIL), and optionally the TIL comprises a tumor infiltrating activated T cell, comprising: detecting the expression or presence of a human LAG-3 protein in or on a cell, tissue or organ sample or portion thereof by contacting the cell, tissue or organ sample with a chimeric or recombinant antibody or antigen binding fragment thereof of claim 1, and detecting whether or not the chimeric or recombinant antibody specifically binds to a human LAG-3 protein in the cell, tissue or organ sample or portion thereof, and the detecting of specific binding indicates the expression or presence of the human LAG-3 protein in the cell, tissue or organ sample, or portion thereof.

* * * * *

SEQUENCE LISTING

```
<160> NUMBER OF SEQ ID NOS: 11

<210> SEQ ID NO 1
<211> LENGTH: 29
<212> TYPE: PRT
<213> ORGANISM: homo sapiens

<400> SEQUENCE: 1

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg
            20                  25

<210> SEQ ID NO 2
<211> LENGTH: 112
<212> TYPE: PRT
<213> ORGANISM: artificial sequence
<220> FEATURE:
<223> OTHER INFORMATION: synthetic polypeptide

<400> SEQUENCE: 2

Gln Ser Val Lys Glu Ser Glu Gly Gly Leu Phe Lys Pro Thr Asp Thr
1               5                   10                  15

Leu Thr Leu Thr Cys Thr Val Ser Gly Ile Asp Leu Ser Ser Gly Ile
            20                  25                  30
```

```
Leu Val Trp Val Arg Gln Ala Pro Gly Ser Gly Leu Glu Trp Ile Gly
         35                  40                  45

Gly Ile Asp Ala Asn Gly Arg Ala Tyr Tyr Ala Ser Trp Ala Lys Ser
 50                  55                  60

Arg Ser Thr Ile Thr Arg Asn Thr Asn Glu Asn Thr Val Thr Leu Lys
 65                  70                  75                  80

Met Thr Ser Leu Thr Ala Ala Asp Thr Ala Thr Tyr Phe Cys Ala Gly
                 85                  90                  95

Gly Ala Trp Asn Ile Trp Gly Pro Gly Thr Leu Val Thr Val Ser Ser
             100                 105                 110
```

<210> SEQ ID NO 3
<211> LENGTH: 113
<212> TYPE: PRT
<213> ORGANISM: artificial sequence
<220> FEATURE:
<223> OTHER INFORMATION: synthetic polypeptide

<400> SEQUENCE: 3

```
Ala Gln Val Leu Thr Gln Thr Pro Ser Pro Val Ser Ala Ala Val Gly
 1               5                  10                  15

Gly Thr Val Thr Ile Lys Cys Gln Ser Ser Gln Ser Val Tyr Asp Ser
                 20                  25                  30

Asn Thr Leu Ala Trp Phe Gln Gln Lys Pro Gly Gln Pro Pro Lys Leu
             35                  40                  45

Leu Met Tyr Ser Ala Ser Thr Leu Ala Phe Gly Val Pro Ser Arg Phe
 50                  55                  60

Ser Gly Ser Gly Ser Gly Thr Gln Phe Thr Leu Thr Ile Ser Asp Leu
 65                  70                  75                  80

Glu Cys Ala Asp Ala Ala Thr Tyr Tyr Cys Leu Gly Ser Tyr Asp Cys
                 85                  90                  95

Ser Ser Val Asp Cys Thr Ala Phe Gly Gly Gly Thr Glu Val Val Val
             100                 105                 110

Lys
```

<210> SEQ ID NO 4
<211> LENGTH: 104
<212> TYPE: PRT
<213> ORGANISM: artificial sequence
<220> FEATURE:
<223> OTHER INFORMATION: synthetic polypeptide

<400> SEQUENCE: 4

```
Gly Asp Pro Gly Ala Pro Thr Val Leu Ile Phe Pro Pro Ala Ala Asp
 1               5                  10                  15

Gln Val Ala Thr Gly Thr Val Thr Ile Val Cys Val Ala Asn Lys Tyr
                 20                  25                  30

Phe Pro Asp Val Thr Val Thr Trp Glu Val Asp Gly Thr Thr Gln Thr
             35                  40                  45

Thr Gly Ile Glu Asn Ser Lys Thr Pro Gln Asn Ser Ala Asp Cys Thr
 50                  55                  60

Tyr Asn Leu Ser Ser Thr Leu Thr Leu Thr Ser Thr Gln Tyr Asn Ser
 65                  70                  75                  80

His Lys Glu Tyr Thr Cys Lys Val Thr Gln Gly Thr Thr Ser Val Val
                 85                  90                  95

Gln Ser Phe Asn Arg Gly Asp Cys
             100
```

```
<210> SEQ ID NO 5
<211> LENGTH: 104
<212> TYPE: PRT
<213> ORGANISM: artificial sequence
<220> FEATURE:
<223> OTHER INFORMATION: synthetic polypeptide

<400> SEQUENCE: 5

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 6
<211> LENGTH: 323
<212> TYPE: PRT
<213> ORGANISM: artificial sequence
<220> FEATURE:
<223> OTHER INFORMATION: synthetic polypeptide

<400> SEQUENCE: 6

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205
```

```
Glu Lys Thr Ile Ser Lys Ala Arg Gly Gln Pro Leu Glu Pro Lys Val
    210                 215                 220
Tyr Thr Met Gly Pro Pro Arg Glu Glu Leu Ser Ser Arg Ser Val Ser
225                 230                 235                 240
Leu Thr Cys Met Ile Asn Gly Phe Tyr Pro Ser Asp Ile Ser Val Glu
                245                 250                 255
Trp Glu Lys Asn Gly Lys Ala Glu Asp Asn Tyr Lys Thr Thr Pro Ala
                260                 265                 270
Val Leu Asp Ser Asp Gly Ser Tyr Phe Leu Tyr Ser Lys Leu Ser Val
            275                 280                 285
Pro Thr Ser Glu Trp Gln Arg Gly Asp Val Phe Thr Cys Ser Val Met
            290                 295                 300
His Glu Ala Leu His Asn His Tyr Thr Gln Lys Ser Ile Ser Arg Ser
305                 310                 315                 320
Pro Gly Lys

<210> SEQ ID NO 7
<211> LENGTH: 217
<212> TYPE: PRT
<213> ORGANISM: artificial sequence
<220> FEATURE:
<223> OTHER INFORMATION: synthetic polypeptide

<400> SEQUENCE: 7

Ala Gln Val Leu Thr Gln Thr Pro Ser Pro Val Ser Ala Ala Val Gly
1               5                   10                  15
Gly Thr Val Thr Ile Lys Cys Gln Ser Ser Gln Ser Val Tyr Asp Ser
                20                  25                  30
Asn Thr Leu Ala Trp Phe Gln Gln Lys Pro Gly Gln Pro Pro Lys Leu
            35                  40                  45
Leu Met Tyr Ser Ala Ser Thr Leu Ala Phe Gly Val Pro Ser Arg Phe
50                  55                  60
Ser Gly Ser Gly Ser Gly Thr Gln Phe Thr Leu Thr Ile Ser Asp Leu
65                  70                  75                  80
Glu Cys Ala Asp Ala Ala Thr Tyr Tyr Cys Leu Gly Ser Tyr Asp Cys
                85                  90                  95
Ser Ser Val Asp Cys Thr Ala Phe Gly Gly Gly Thr Glu Val Val Val
                100                 105                 110
Lys Gly Asp Pro Gly Ala Pro Thr Val Leu Ile Phe Pro Pro Ala Ala
            115                 120                 125
Asp Gln Val Ala Thr Gly Thr Val Thr Ile Val Cys Val Ala Asn Lys
130                 135                 140
Tyr Phe Pro Asp Val Thr Val Thr Trp Glu Val Asp Gly Thr Thr Gln
145                 150                 155                 160
Thr Thr Gly Ile Glu Asn Ser Lys Thr Pro Gln Asn Ser Ala Asp Cys
                165                 170                 175
Thr Tyr Asn Leu Ser Ser Thr Leu Thr Leu Thr Ser Thr Gln Tyr Asn
                180                 185                 190
Ser His Lys Glu Tyr Thr Cys Lys Val Thr Gln Gly Thr Thr Ser Val
            195                 200                 205
Val Gln Ser Phe Asn Arg Gly Asp Cys
            210                 215

<210> SEQ ID NO 8
<211> LENGTH: 217
```

<212> TYPE: PRT
<213> ORGANISM: artificial sequence
<220> FEATURE:
<223> OTHER INFORMATION: synthetic polypeptide

<400> SEQUENCE: 8

Ala Gln Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Asp Ser
            20                  25                  30

Asn Thr Leu Ala Trp Phe Gln Gln Lys Pro Gly Gln Pro Pro Lys Leu
        35                  40                  45

Leu Met Tyr Ser Ala Ser Thr Leu Ala Phe Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Ala Asp Ala Ala Thr Tyr Tyr Cys Leu Gly Ser Tyr Asp Cys
                85                  90                  95

Ser Ser Val Asp Cys Thr Ala Phe Gly Gly Thr Glu Val Val Val
            100                 105                 110

Lys Gly Asp Pro Val Ala Pro Thr Val Leu Ile Phe Pro Pro Ala Ala
        115                 120                 125

Asp Gln Val Ala Thr Gly Thr Val Thr Ile Val Cys Val Ala Asn Lys
    130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Thr Pro Gln Asn Ser Ala Asp Cys
                165                 170                 175

Thr Tyr Asn Leu Ser Ser Thr Leu Thr Leu Thr Ser Thr Gln Tyr Asn
            180                 185                 190

Ser His Lys Glu Tyr Thr Cys Lys Val Thr Gln Gly Thr Thr Ser Val
        195                 200                 205

Val Gln Ser Phe Asn Arg Gly Asp Cys
    210                 215

<210> SEQ ID NO 9
<211> LENGTH: 435
<212> TYPE: PRT
<213> ORGANISM: artificial sequence
<220> FEATURE:
<223> OTHER INFORMATION: synthetic polypeptide

<400> SEQUENCE: 9

Gln Ser Val Lys Glu Ser Glu Gly Gly Leu Phe Lys Pro Thr Asp Thr
1               5                   10                  15

Leu Thr Leu Thr Cys Thr Val Ser Gly Ile Asp Leu Ser Ser Gly Ile
            20                  25                  30

Leu Val Trp Val Arg Gln Ala Pro Gly Ser Gly Leu Glu Trp Ile Gly
        35                  40                  45

Gly Ile Asp Ala Asn Gly Arg Ala Tyr Tyr Ala Ser Trp Ala Lys Ser
    50                  55                  60

Arg Ser Thr Ile Thr Arg Asn Thr Asn Glu Asn Thr Val Thr Leu Lys
65                  70                  75                  80

Met Thr Ser Leu Thr Ala Ala Asp Thr Ala Thr Tyr Phe Cys Ala Gly
                85                  90                  95

Gly Ala Trp Asn Ile Trp Gly Pro Gly Thr Leu Val Thr Val Ser Ser
            100                 105                 110

```
Gly Gln Pro Lys Ala Pro Ser Val Phe Pro Leu Ala Pro Cys Cys Gly
            115                 120                 125
Asp Thr Pro Ser Ser Thr Val Thr Leu Gly Cys Leu Val Lys Gly Tyr
        130                 135                 140
Leu Pro Glu Pro Val Thr Val Thr Trp Asn Ser Gly Thr Leu Thr Asn
145                 150                 155                 160
Gly Val Arg Thr Phe Pro Ser Val Arg Gln Ser Ser Gly Leu Tyr Ser
                165                 170                 175
Leu Ser Ser Val Val Ser Val Thr Ser Ser Gln Pro Val Thr Cys
            180                 185                 190
Asn Val Ala His Pro Ala Thr Asn Thr Lys Val Asp Lys Thr Val Ala
            195                 200                 205
Pro Ser Thr Cys Ser Lys Pro Thr Cys Pro Pro Pro Glu Leu Leu Gly
        210                 215                 220
Gly Pro Ser Val Phe Ile Phe Pro Pro Lys Pro Lys Asp Thr Leu Met
225                 230                 235                 240
Ile Ser Arg Thr Pro Glu Val Thr Cys Val Val Val Asp Val Ser Gln
                245                 250                 255
Asp Asp Pro Glu Val Gln Phe Thr Trp Tyr Ile Asn Asn Glu Gln Val
            260                 265                 270
Arg Thr Ala Arg Pro Pro Leu Arg Glu Gln Gln Phe Asn Ser Thr Ile
        275                 280                 285
Arg Val Val Ser Thr Leu Pro Ile Ala His Gln Asp Trp Leu Arg Gly
        290                 295                 300
Lys Glu Phe Lys Cys Lys Val His Asn Lys Ala Leu Pro Ala Pro Ile
305                 310                 315                 320
Glu Lys Thr Ile Ser Lys Ala Arg Gly Gln Pro Leu Glu Pro Lys Val
                325                 330                 335
Tyr Thr Met Gly Pro Pro Arg Glu Glu Leu Ser Ser Arg Ser Val Ser
            340                 345                 350
Leu Thr Cys Met Ile Asn Gly Phe Tyr Pro Ser Asp Ile Ser Val Glu
        355                 360                 365
Trp Glu Lys Asn Gly Lys Ala Glu Asp Asn Tyr Lys Thr Thr Pro Ala
        370                 375                 380
Val Leu Asp Ser Asp Gly Ser Tyr Phe Leu Tyr Ser Lys Leu Ser Val
385                 390                 395                 400
Pro Thr Ser Glu Trp Gln Arg Gly Asp Val Phe Thr Cys Ser Val Met
                405                 410                 415
His Glu Ala Leu His Asn His Tyr Thr Gln Lys Ser Ile Ser Arg Ser
            420                 425                 430
Pro Gly Lys
        435

<210> SEQ ID NO 10
<211> LENGTH: 8
<212> TYPE: PRT
<213> ORGANISM: artificial sequence
<220> FEATURE:
<223> OTHER INFORMATION: synthetic polypeptide

<400> SEQUENCE: 10

Trp Ser His Pro Gln Phe Glu Lys
1               5

<210> SEQ ID NO 11
```

```
<211> LENGTH: 8
<212> TYPE: PRT
<213> ORGANISM: artificial sequence
<220> FEATURE:
<223> OTHER INFORMATION: synthetic polypeptide

<400> SEQUENCE: 11

Asp Tyr Lys Asp Asp Asp Asp Lys
1               5
```